(12) United States Patent
Williams et al.

(10) Patent No.: US 9,096,844 B2
(45) Date of Patent: Aug. 4, 2015

(54) PHOTOCLEAVABLE LINKER

(71) Applicant: City of Hope, Duarte, CA (US)

(72) Inventors: John C. Williams, Duarte, CA (US); David Horne, Duarte, CA (US); Jun Xie, Duarte, CA (US); Shubbir Ahmed, Duarte, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 14/083,938

(22) Filed: Nov. 19, 2013

(65) Prior Publication Data
US 2014/0154775 A1  Jun. 5, 2014

Related U.S. Application Data

(60) Provisional application No. 61/728,138, filed on Nov. 19, 2012.

(51) Int. Cl.
*C12N 9/96* (2006.01)
*C12N 9/90* (2006.01)
*C12N 9/00* (2006.01)

(52) U.S. Cl.
CPC .. *C12N 9/96* (2013.01); *C12N 9/90* (2013.01); *C12N 9/93* (2013.01); *C12Y 502/01008* (2013.01)

(58) Field of Classification Search
CPC .............. C12N 9/90; C12N 9/93; C12N 9/96; C12Y 502/01008
See application file for complete search history.

(56) References Cited

PUBLICATIONS

Spencer, D. M. et al. Controlling Signal Transduction with Synthetic Ligands, Science, 1993, 262, 1019-1024.*
D. Varma, et al., 2010, *Proc Natl Acad Sci U S A* 107:3493.
J. C. Williams, et al., 2007, *Proc Nad Acad Sci U S A* 104:10028.
W. Yang, et al., 2000, *J Med Chem* 43, 1135.
A. M. Piggott & P. Karuso, 2005, *Molecules* 10:1292.
N. Umeda, et al., 2011, *J Am Chem Soc* 133:12.
R. DeRose, et al., 2012, *J Vis Exp 2012*.
U.S. Appl. No. 61/728,138, filed Nov. 19, 2012.

* cited by examiner

*Primary Examiner* — Gina Justice
*Assistant Examiner* — Genevieve S Alley
(74) *Attorney, Agent, or Firm* — Mintz Levin Cohn Ferris Glovsky and Popeo PC

(57) ABSTRACT

There are provided, inter alia, photolabile compounds and methods useful for the formation of dimers of biological molecules and subsequent dissociation of the dimers.

19 Claims, 23 Drawing Sheets

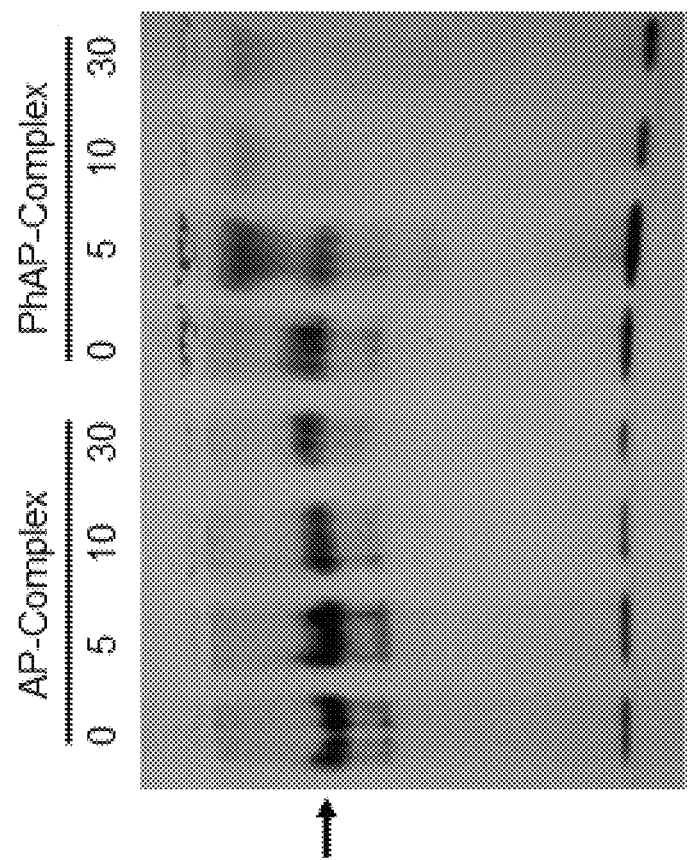
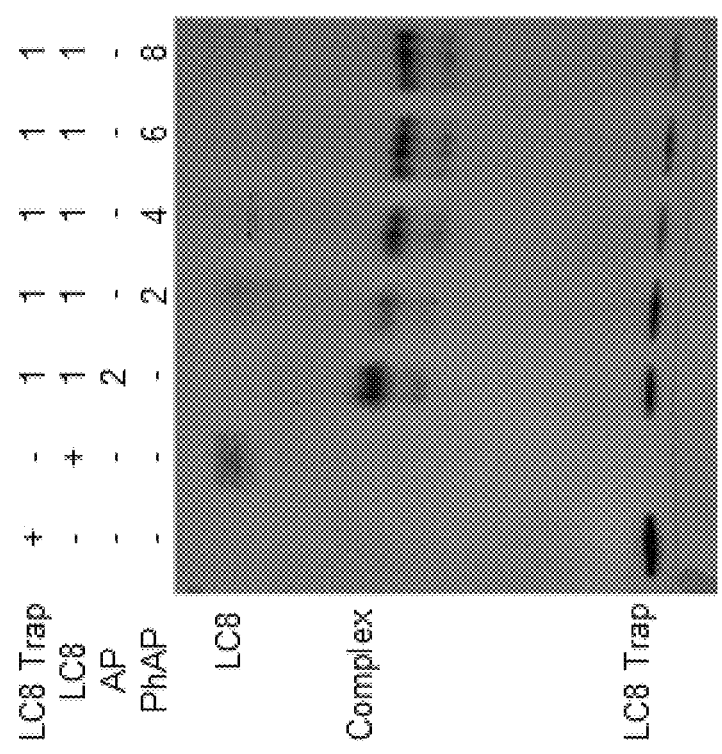
FIG. 2C
FIG. 2A

Chemical Formula: $C_{86}H_{103}N_3NaO_{24}^+$
Exact Mass: 1584.6824
m/z: 1584.6829 (100.0%), 1585.6963 (93.0%),
1586.6896 (42.8%), 1587.6930 (12.9%)

Chemical Formula: $C_{67}H_{76}N_2NaO_{18}^+$
Exact Mass: 1219.50

Chemical Formula: $C_{48}H_{58}N_2NaO_{14}^+$
Exact Mass: 909.3780

Chemical Formula: $C_{48}H_{56}N_2NaO_{13}^+$
Exact Mass: 891.3675

Chemical Formula: $C_{48}H_{49}NNaO_{12}{}^+$
Exact Mass: 854.3137

Chemical Formula: $C_{86}H_{103}N_3Na_2O_{24}{}^{2+}$
Exact Mass: 1607.6716

Chemical Formula: $C_{38}H_{47}NNaO_{11}^{+}$
Exact Mass: 716.3041

Chemical Formula: $C_{19}H_{27}NNaO_{6}^{+}$
Exact Mass: 388.1731

Chemical Formula: $C_{13}H_{18}NaO_{5}^{+}$
Exact Mass: 277.1046

Round 1    fkbp-RGPIKLGMAKITQVDFPPR*

Round 2    fkbp-RGPIKAGMAKITQVDFPPR*

Round 3    fkbp-RGGGSAGMAKITQVDFPPR*

```
                         SEQUENCE LISTING

<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified by bond to FKBP

<400> SEQUENCE: 1

Gly Gly Ser Gly Thr Tyr Thr Lys Glu Thr Gln Thr Pro
1               5                   10

<210> SEQ ID NO 2
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified by bond to FKBP

<400> SEQUENCE: 2

Arg Gly Pro Ile Lys Leu Gly Met Ala Lys Ile Thr Gln Val Asp Phe
1               5                   10                  15
```

```
Pro Pro Arg

<210> SEQ ID NO 3
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue 1 modified by bond to FKBP

<400> SEQUENCE: 3

Arg Gly Pro Ile Lys Ala Gly Met Ala Lys Ile Thr Gln Val Asp Phe
1               5                   10                  15

Pro Pro Arg

<210> SEQ ID NO 4
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 4

Arg Gly Gly Gly Ser Ala Gly Met Ala Lys Ile Thr Gln Val Asp Phe
1               5                   10                  15

Pro Pro Arg

<210> SEQ ID NO 5
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 5

Arg Glu Ile Val Thr Tyr Thr Lys Glu Thr Gln Thr Pro
1               5                   10
```

PHOTOCLEAVABLE LINKER

CROSS-REFERENCES TO RELATED APPLICATIONS

This application claims the benefit of U.S. Provisional Application No. 61/728,138, filed Nov. 19, 2012, the content of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under NS071166-01 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 95058-887882_ST25.TXT, created on Nov. 7, 2013, 1,869 bytes, machine format IBM-PC, MS Windows operating system, is hereby incorporated by reference.

BACKGROUND OF THE INVENTION

The ability to rapidly and specifically regulate the activity of selected proteins and macromolecular complexes is essential to parse out critical functions in complicated macromolecular systems (e.g., signal transduction, protein trafficking, cell division). See e.g., J. E. Rothman, *Mol Biol Cell* 2010, 21, 3776; C. Brieke, et al., 2012, *Angew Chem Int Ed Engl* 2012, 51:8446. In combination with functional assays such as imaging, immunoprecipitation, western blot analysis, RT-PCR, and the like, perturbing the function of specific proteins of interest can reveal novel associations, critical post-translation modifications, and up-stream and down-stream effectors. Although small molecule inhibitors exist that lend themselves to such analyses (e.g., protein kinase, histone deacetylase, protease, and G protein-coupled receptor inhibitors), the actions of most of these inhibitors are primarily focused on a small subset of enzymes that are frequently therapeutic targets. In fact, only 2% of all predicted human gene products (mostly kinases) have been successfully targeted with small molecules, and it is estimated that only 10-15% of the human genome is 'druggable.' See e.g., S. J. Dixon & B. R. Stockwell, 2009, *Curr Opin Chem Biol* 13:549. Thus, there is a tremendous gap in that only a handful of gene products can be studied using small molecule inhibitors, while there is a paucity of useful inhibitors for the remaining 85-90% of gene products.

The limited number of novel small molecule inhibitors stems from multiple sources and is partially because a large number of gene products act as components of macromolecular complexes and bind to their respective target(s) through extended surface contacts. The binding affinity and specificity for these interactions arise through multiple weak interactions, and the protein targets frequently lack a deep, solvent occluded cleft as is typically found in enzymes. See e.g., K. Sugase, et al., 2007, *Nature* 447, 1021; V. N. Uversky, et al., 2005, *J Mol Recognit* 18:343. Moreover, many proteins share common domains, and thus potential inhibitors may target a common domain and therefore could lack the required specificity and produce off-target effects.

Provided herein are compositions and methods addressing these and other needs in the art.

BRIEF SUMMARY OF THE INVENTION

Provided herein, inter alia, are novel photocleavable compounds that, upon cleavage, frees the 'targeted' endogenous ligand, and permits disruption of a biochemical process and follow its return to equilibrium.

In a first aspect, there is provided a compound having the structure of Formula (I):

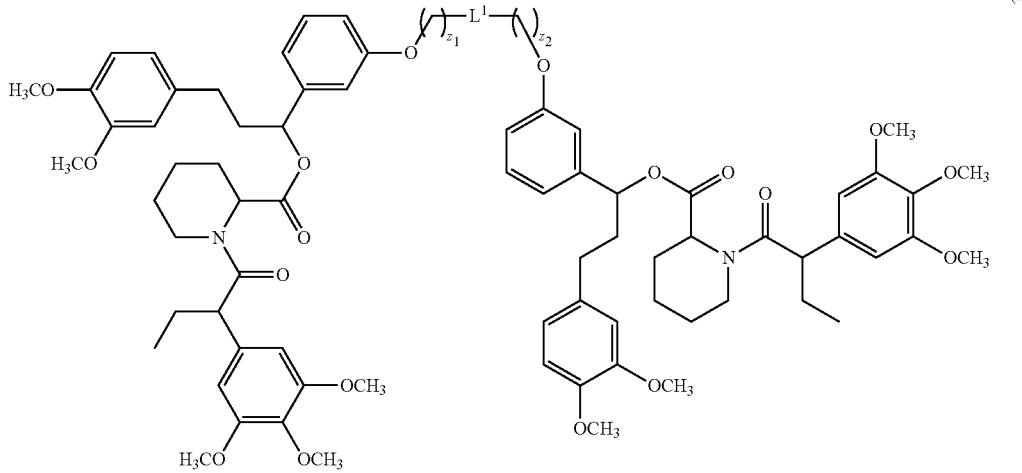

wherein, $L^1$ is a photocleavable linker, and $z_1$ and $z_2$ are each independently an integer in the range 0 to 6.

In another aspect, there is provided a method of forming an FK506 binding protein (FKBP) dimer. The method includes contacting a first FKBP and a second FKBP with the compound of Formula I, and allowing the compound to bind to the first FKBP and the second FKBP, thereby forming an FKBP dimer which includes a link between the first FKBP and the second FKBP.

BRIEF DESCRIPTION OF THE DRAWINGS

FIG. 2A: Native PAGE analysis of PhAP activity. LC8 migrates near the front of the gel. The LC8 trap monomer (i.e., FKBP-IC peptide) is positively charged and does not enter the gel. A complex forms, when a mix of equimolar concentration of LC8 and LC8$_{TRAP}$ is treated with different molar concentration of AP or PhAP (1×, 2× etc.) FIG. 2C: Native PAGE analysis of LC8-LC8$_{TRAP}$ complexes formed using AP or PhAP and exposed to UV light (350 nm) for the indicated times (min).

FIG. 3A: Cos1 cells were transiently transfected with EGFP-LC8$_{TRAP}$ and treated with AP or PhAP for pre-determined periods (0.5 h, 1 h. and 2 h), exposed to UV light, and then fixed and stained with an anti-EEA1 antibody. Fluorescence microscopy was used to quantify the activity of the AP or PhAP on endosomes dispersion. Each data point reflects 100 cells (n=3). FIG. 3B: Fluorescence microscopic images showing the endosomes dispersion when treated with PhAP (right) or AP (left). Cells containing compact endosomes (marked C) or dispersed endosomes (marked D) and those harboring the trap (fluorescence) were clearly distinguishable. Cells not transfected with the trap (no GFP) serve as a negative controls (data not shown).

FIG. 10A: Schematic of LC8-trap construct. Sequence legend: SEQ ID NO:1. FIG. 10B: Native PAGE analysis indicating that dimerization of the LC8-trap leads to stoichiometric complex formation. Note that the LC8-trap migrates in the opposite direction of LC8, runs into the negative pole and produces a faint band at the buffer strip. The admixture of LC8 and the LC8-trap without the dimerization agent, AP20187, does not cause a shift in the LC8 band (lane 5). However, the addition of AP20187 produces a new band that migrates midway down the gel (lanes 6-8). Molar ratios of 1:½, 1:1 and 1:2 of LC8 and the LC8-trap, respectively, show the interaction is stoichiometric. FIG. 10C: Representative size exclusion chromatography (SEC) traces show the formation of a new complex at an earlier elution volume, obtained only in the presence of AP20187. FIG. 10D: Schematic of the three iterations required to achieve low affinity between the monomeric TcTex-trap and TcTex1 while retaining high affinity upon dimerization. The point mutations in the dynein IC sequence necessary to achieve this are shown for each iteration. Sequence legend (in order): SEQ ID NOS:2-4. FIG. 10E: SEC traces of the various TcTex-traps, with and without AP20187. TcTex1 and the initial TcTex-trap sequence formed a stable complex in the absence of AP20187. In round 2, the point mutant, L112A, effectively reduced the affinity of the interaction, but required significantly higher concentrations of AP20187 to form the complex. In round 3, the residues between FKBP and the TcTex1 binding site were mutated to flexible, hydrophilic residues.

FIG. 11A: Native PAGE analysis of the IC trap at 25° C. Unlike the LC8 trap, the IC trap readily enters the gel (Lane 1). Dimerization of the IC trap by AP20187 (AP) alters its motility. The addition of dynein IC, residues 1-44, to the dimerized IC trap produces a band midway down the gel, indicative of a complex. In the absence of AP20187, no shift is observed (e.g., the band in lane 4 is equivalent to that in lane 1). Finally, the dynein IC is positively charged and runs in the opposite direction, and therefore is not seen in the gel (lanes 5 and 6). FIG. 11B: CD spectrum of the IC trap and AP20187 using a split cell. Squares, before mixing; triangles after mixing. FIG. 11C: CD spectrum of the IC trap, the IC and AP20187 using a split cell. Squares, before mixing; triangles after mixing. Note there is a substantial increase in the helicity after mixing, suggesting the IC undergoes a significant disorder-to-order transition upon binding the dimerized IC trap.

(FIG. 12A) Cells stained with the EEA1 marker to visualize endosomes. (FIG. 12B) Cells stained with LAMP2 marker to visualize lysosomes. (FIG. 12C) Cells stained with GM130 marker to detect Golgi bodies. Cells with dispersed vesicles are marked with a "d". Note that the endosomes and lysosomes in non-transfected cells remain compact (marked with a "c").

FIG. 14A: The left panel shows the number of cells with dispersed lysosomes (dotted lines), endosomes (dashed lines) or Golgi (dash-dot-dot lines) induced by dimerization of the LC8-trap (open circles) or TcTex1-trap (open triangles) plotted as a function of time after the induction of dimerization of AP20187. Shown as a control is the dispersion of Golgi bodies in cells expressing GFP-FKBP. FIG. 14B: The right panel shows the number of cells with dispersed endosomes (dashed lines) or Golgi (dash-dot-dot lines) induced by dimerization of the IC trap. The controls are the same experiments, but using GFP-FKBP instead of the trap. Each data point represents 3 independent measurements of 100 transfected cells for each trap or control (standard deviation for each data point is shown as a bar).

DETAILED DESCRIPTION OF THE INVENTION

I. Definitions

Figure 1:
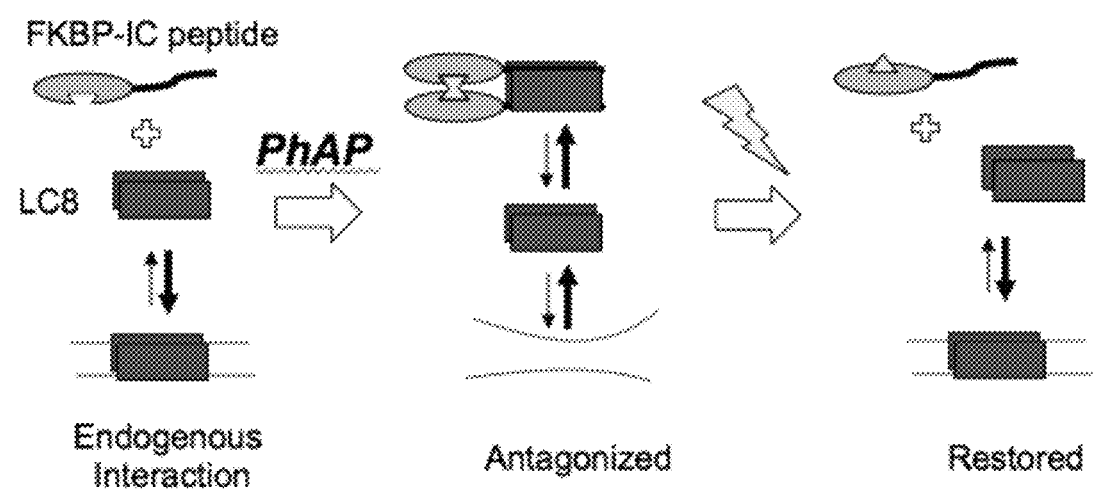
FIG. 1 depicts molecular trapping which uses the chemically-induced dimerization of FKBP to create a bivalent, high affinity ligand to either sequester an endogenous protein or directly antagonize an interface. In this case, the dynein intermediate chain (IC) peptide, which binds to LC8 with low affinity as a monomer, is fused to FKBP. The addition of photocleavable AP analog PhAP (triangular depiction) creates a high affinity trap that binds to LC8, competes with endogenous ligands (IC, depicted as lines), and induces phenotypes associated with dynein antagonism (e.g., endosome dispersion). The multivalent complex is highly stable. Creation of a photocleavable dimerizer (PhAP) can facilitate the dissociation and reverse the antagonism after exposure to UV light.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, unless otherwise stated, mean cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2 m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O) $CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O) NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The terms "linkage," "linker," "link" and the like as used herein refer to a first moiety (e.g., a photocleavable linker) bonded to two other moieties, wherein the two other moieties are linked via the first moiety. In some embodiments a "linkage" or "linker" may include an ether (—O—), a carbonyl (—C(O)—), an amino (—NH—), an amido (—N—C(O)—), a thio (—S—), a phospho (—O—P(X)(OR)—O— wherein X is O or S; and R is hydrogen, substituted or unsubstituted alkyl, substituted or unsubstituted aryl), an ester (—C(O)O—), a carbonate (—OC(O)O—), a carbamate (—OC(O)NH—), or a thiono (—C(S)—). In one embodiment, the "linker" refers to a moiety that links two amino groups. In one embodiment, the "linker" refers to a moiety that links two alkyloxy functionalities. In one embodiment, the "linker" is a photocleavable linker, as known in the art.

As used herein, the term "FKBP" refers to the family of FK506 binding proteins having prolyl isomerase activity. The term FKBP includes, for example, FKBP12 as well as proteins encoded by the genes AIP; AIPL1; FKBP1A; FKBP1B; FKBP2; FKBP3; FKBP5; FKBP6; FKBP7; FKBP8; FKBP9; FKBP9L; FKBP10; FKBP11; FKBP14; FKBP15; FKBP52; and LOC541473; including homologs thereof and functional protein fragments thereof.

II. Compounds

In a first aspect, there is provided a compound having the structure of Formula (I):

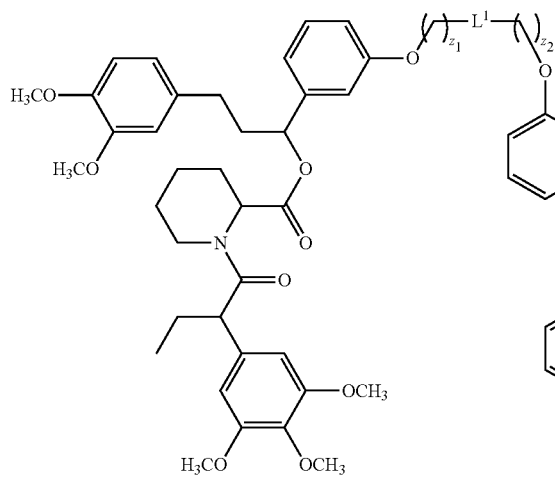 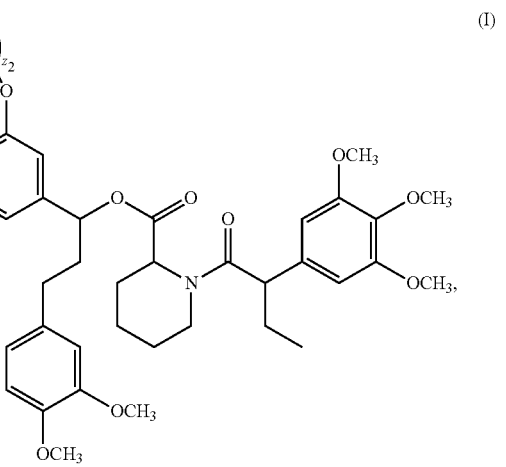

(I)

wherein, $L^1$ is a photocleavable linker, and $z_1$ and $z_2$ are each independently an integer in the range 0 to 6.

In one embodiment, z1 and z2 are each independently an integer in the range 1 to 6 In one embodiment, z1 and z2 are each independently an integer in the range 1 to 3. In one embodiment, z1 is 0, 1, 2, 3, 4, 5, or 6, and z2 is 0, 1, 2, 3, 4, 5 or 6. In one embodiment, z1 is 0, 1, 2 or 3, and z2 is 0, 1, 2 or 3. In one embodiment, z1 is 1, and z2 is 1.

In one embodiment, the compound of Formula (I) has the structure of Formula (Ia) following, wherein z1 and z2 are independently 1:

In one embodiment, $L^1$ includes a nitrophenylene moiety.
In one embodiment, $L^1$ has the formula $$-L^2-L^3-L^4-L^5-L^6-  \quad \text{Formula (II)},$$

wherein $L^2$ and $L^6$ are independently —C(O)O—; $L^3$ and $L^5$ are independently a bond or substituted or unsubstituted alkylene; $L^4$ is $R^1$-substituted arylene; and $R^1$ is an electron withdrawing group. In one embodiment, $L^1$ has the formula —C(O)O-$L^3$-$L^4$-$L^5$-C(O)O— (Formula IIa).

In embodiments, $R^1$ is halogen, —NO$_2$, —N$^+$(R$^2$)$_3$, —SR$^2$, —OR$^2$, —N(R$^2$)$_2$, —CF$_3$, —CCl$_3$, —CN, —SO$_3$R$^2$,

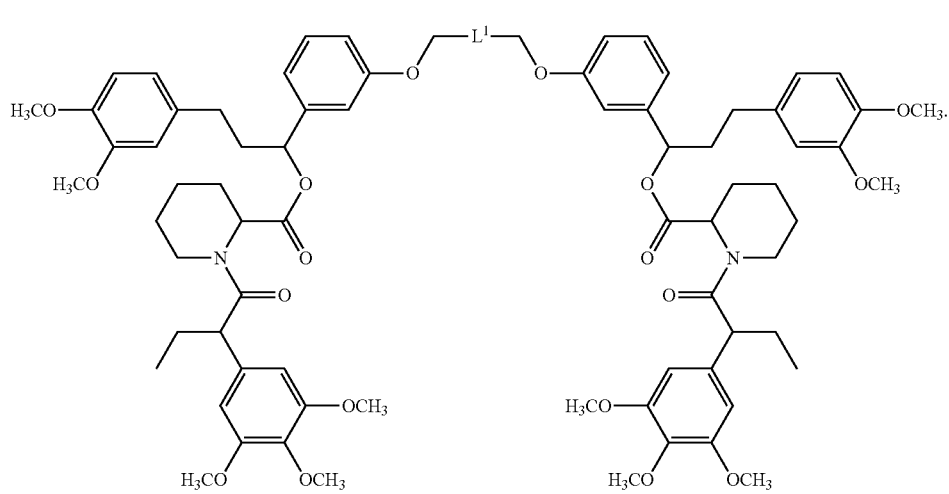

(Ia)

In one embodiment, $L^1$ of the compound of Formula (I) is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In one embodiment, $L^1$ is substituted alkylene, substituted heteroalkylene, substituted cycloalkylene, substituted heterocycloalkylene, substituted arylene or substituted heteroarylene. In one embodiment, $L^1$ is unsubstituted alkylene, unsubstituted heteroalkylene, unsubstituted cycloalkylene, unsubstituted heterocycloalkylene, unsubstituted arylene or unsubstituted heteroarylene.

—COOR$^2$, —CHO or —COR$^2$, substituted or unsubstituted alkyl, substituted or unsubstituted heteroalkyl, substituted or unsubstituted cycloalkyl, substituted or unsubstituted heteroaryl, or substituted or unsubstituted aryl. In embodiments, $R^1$ is halogen, —NO$_2$, —N$^+$(R$^2$)$_3$, —SR$^2$, —OR$^2$, —N(R$^2$)$_2$, —CF$_3$, —CCl$_3$, —CN, —SO$_3$R$^2$, —COOR$^2$, —CHO, —COR$^2$, R$^2$-substituted or unsubstituted alkyl, R$^2$-substituted or unsubstituted heteroalkyl, R$^2$-substituted or unsubstituted cycloalkyl, R$^2$-substituted or unsubstituted heterocycloalkyl, R$^2$-substituted or unsubstituted heteroaryl, or R$^2$-substituted or unsubstituted aryl. $R^2$ is hydrogen, halogen, —NO$_2$, —NH$_2$, —CF$_3$, —CCl$_3$, —CN, —SO$_3$H, —COOH, —CHO, —CONH₂, —OH, —SH, —NHCO₂H, substituted or unsubstituted alkyl, substituted or unsubstituted heteroalkyl, substituted or unsubstituted cycloalkyl, substituted or unsubstituted heterocycloalkyl, substituted or unsubstituted heteroaryl, or substituted or unsubstituted aryl. In one embodiment, $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, or substituted or unsubstituted aryl. In one embodiment, $R^2$ is hydrogen, halogen, —NO₂, —NH₂, —CF₃, —CCl₃, —CN, —SO₃H, —COOH, —CHO, —CONH₂, —OH, —SH, —NHCO₂H, $R^3$-substituted or unsubstituted alkyl, $R^3$-substituted or unsubstituted heteroalkyl, $R^3$-substituted or unsubstituted cycloalkyl, $R^3$-substituted or unsubstituted heterocycloalkyl, $R^3$-substituted or unsubstituted heteroaryl, or $R^3$-substituted or unsubstituted aryl. In one embodiment, $R^2$ is hydrogen, $R^3$-substituted or unsubstituted alkyl, $R^3$-substituted or unsubstituted heteroalkyl, $R^3$-substituted or unsubstituted cycloalkyl, $R^3$-substituted or unsubstituted heterocycloalkyl, $R^3$-substituted or unsubstituted heteroaryl, or $R^3$-substituted or unsubstituted aryl. $R^3$ is hydrogen, halogen, —NO₂, —NH₂, —CF₃, —CCl₃, —CN, —SO₃H, —COOH, —CHO, —CONH₂, —OH, —SH, —NHCO₂H, unsubstituted alkyl, unsubstituted heteroalkyl, unsubstituted cycloalkyl, unsubstituted heterocycloalkyl, unsubstituted heteroaryl, or unsubstituted aryl. $R^1$ may be halogen, —NO₂, —N⁺($R^2$)₃, —CF₃, —CCl₃, —CN, —SO₃H, —COOH, —CHO or —COR²; and $R^2$ is a substituted or unsubstituted alkyl. $R^1$ may be halogen, —NO₂, —N⁺($R^2$)₃, —CF₃, —CCl₃, —CN, —SO₃H, —COOH, —CHO or —COR²; and $R^2$ is an unsubstituted $C_1$ to $C_4$ alkyl. In one embodiment, $R^1$ is —NO₂. In one embodiment, $R^2$ is a substituted alkyl. In one embodiment, $R^2$ is an unsubstituted alkyl. In one embodiment, $R^2$ is an $R^3$-substituted alkyl, wherein $R^3$ is halogen, unsubstituted alkyl or unsubstituted heteroalkyl. In one embodiment, $R^2$ is unsubstituted alkyl. In one embodiment, $R^2$ is unsubstituted $C_1$ to $C_4$ alkyl. In one embodiment, $R^2$ is methyl.

In one embodiment, $L^1$ is

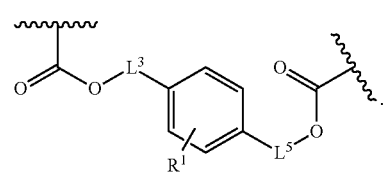

(IIIa)

In Formula (IIIa), $L^3$, $R^1$ and $L^5$ are as defined above. Further to this embodiment, $L^3$ and $L^5$ may independently be substituted or unsubstituted alkylene. $L^3$ and $L^5$ may also independently be substituted or unsubstituted $C_1$ to $C_4$ alkylene. In some embodiments, $L^3$ and $L^5$ are independently substituted or unsubstituted $C_1$ to $C_3$ alkylene. In certain embodiments, $L^3$ and $L^5$ are substituted with an unsubstituted $C_1$ to $C_4$ alkylene. $L^3$ and $L^5$ may be substituted with a methyl. In some embodiments, $L^3$ and $L^5$ are methylene substituted with an unsubstituted $C_1$ to $C_4$ alkylene.

In one embodiment, $L^1$ is

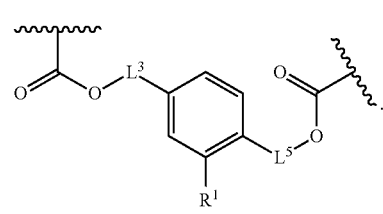

(IIIb)

In Formula (IIIa), $L^3$, $R^1$ and $L^5$ are as defined above. $R^1$ may be NO₂.

In another embodiment, the compound of Formula (I) has the structure of Formula (IV) following:

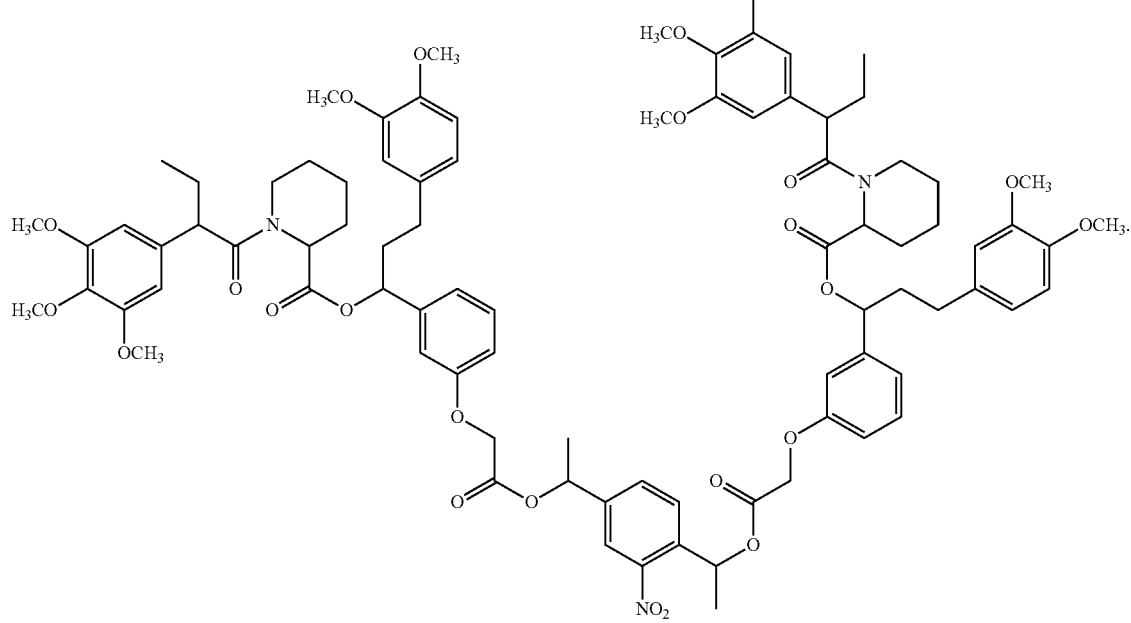

(IV)

The compound of Formula (I) may also have structure of Formula (V) following:

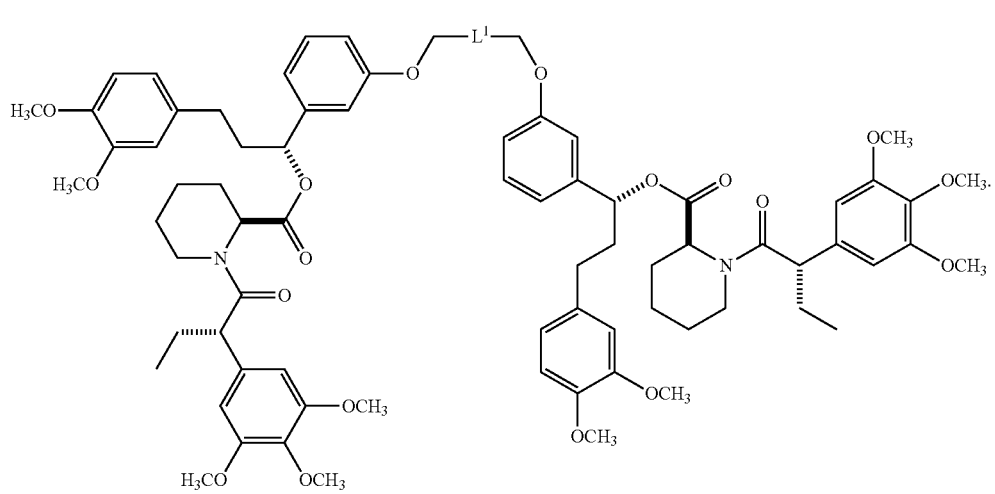

(V)

In one embodiment, the compound of Formula (I) has the structure of Formula (VI) following:

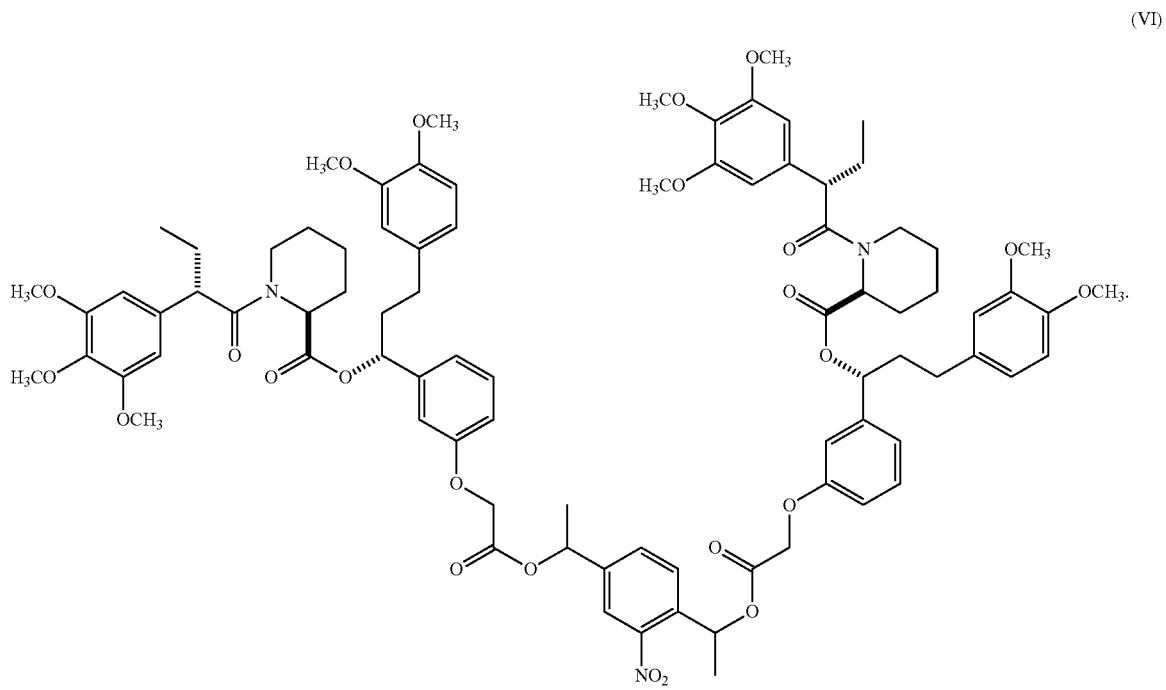

(VI)

III. Methods of Use

In another aspect, there is provided a method of forming an FK506 binding protein (FKBP) dimer. The method includes contacting a first FKBP and a second FKBP with the compound of Formula (I) (including embodiments thereof), and allowing the compound to bind to the first FKBP and the second FKBP, thereby forming an FKBP dimer, and thus a link between the first FKBP and the second FKBP to form a FKBP dimer.

The terms "FK506 binding protein," "FKBP" and the like refer in the usual and customary sense to a family of proteins having prolyl isomerase activity and typically belong in the immunophilin family. It is believed that FKBP does not dimerize under normal physiological conditions, but that dimerization can proceed in the presence of dimerization agents, including, e.g., analogs of FK506 (i.e., tacrolimus) as known in the art.

In one embodiment, the method further includes exposing the FKBP dimer to a photon thereby cleaving the link between the first FKBP and the second FKBP.

In one embodiment, the FKBP is fused to a peptide. In one embodiment, the peptide is a dynein intermediate chain (IC) peptide, or fragment or analog thereof. In one embodiment, the IC peptide binds to LC8. In one embodiment, the peptide is a dynein intermediate chain IC2C peptide, or analog or fragment thereof, which binds to TcTex1. In one embodiment, the FKBP fused to a peptide forms a molecular trap. The terms "molecular trap" and the like refer to fusion products of FKBP and a peptide as disclosed herein, or fragment or analog thereof useful to either sequester an endogenous protein or directly antagonize an interface. In one embodiment, the addition of a compound of Formula (I) (including embodiments thereof), creates a high affinity trap that binds to an endogenous protein (e.g., LC8 or TcTex1), competes with endogenous ligands (e.g., IC or IC2C), and induces phenotypes associated with dynein antagonism (e.g., endosome dispersion).

In one embodiment, the high affinity trap is disrupted by exposing the FKBP dimer to a photon thereby cleaving the link between the first FKBP and the second FKBP.

In one embodiment, the FKBP fused to a peptide is further modified by a reporting group. The term "reporting group" refers in the usual and customary sense to a moiety which provides an indication of the presence and/or location of a compound to which it is attached. In one embodiment, a reporting group may be a dye (e.g., absorbent or fluorescent dye) or a radioactive moiety, as known in the art. In one embodiment, the reporting group is a protein. In one embodiment, the reporting group is green fluorescent protein, as known in the art.

In one embodiment, dimerization of a dynein light chain LC8 or TcTex1 molecular trap affects dynein-associated processes. In one embodiment, endosome dispersion is increased. In one embodiment, lysosome dispersion is increased. In one embodiment, Golgi dispersion is increased. In one embodiment, the maximum dispersion depends on the concentration of the dimerized molecular trap. In one embodiment, maximum dispersion is observed at 1, 2, 3, 4, 5, 6, 7, 8, 9, 10, 20, 30, 40, 50, 100, 200, 300, 400, 500, 600, 700, 800, 900, 1000 nM, or even greater. In one embodiment, the maximum dispersion is observed at about 500 nM of the dimerized molecular trap.

In one embodiment, the extent of endosome dispersion is monitored by assaying the level of early endosome marker 1 (EEA1). In one embodiment, the extent of Golgi dispersion is monitored by assaying with the GM130 marker, as known in the art.

In one embodiment, photocleavage of a compound of Formula (I) (including embodiment thereof) within a molecular trap leads to dissociation and rapid reversal of endosome dispersion.

In one embodiment, methods disclosed herein are useful for measurement of cytoplasmic dynein functions that are distinct from vesicular transport. In one embodiment, mitotic behavior is assayed in cells expressing either the LC8- or TcTex1-traps.

In one embodiment, methods disclosed herein are useful to investigate the role of the dynein LCs in cargo recruitment and regulation of dynein activity. Accordingly, in one embodiment, an LC8 binding region of dynein IC is fused to the C-terminus of FKBP. In one embodiment, a TcTex1 binding region of dynein Ic2C is fused to the C-terminus of FKBP.

In one embodiment, methods disclosed herein are useful to determine the in vivo effect of dynein LC and IC traps. In one embodiment, green fluorescent protein (GFP) can be fused to the N-terminus of FKBP-traps to identify transfected cells. In one embodiment, Cos1, Cos7, or HeLa cells can be transfected with either trap or a GFP-FKBP control. In one embodiment, endosomes, lysosomes and Golgi can be labeled with EEA1, LAMP2 and GM130 markers, respectively. In one embodiment, cells that expressed either trap can be treated with a compound of Formula (I) (including embodiments thereof).

In one embodiment, the fraction of cells with dispersed organelles, as a result of the methods disclosed herein, is observed as a function of time, in order to cause immediate inhibition of protein function and follow the cellular response from this perturbation.

IV. Examples

We have developed, inter alia, chemically-induced molecular traps that use the cell-permeable, small molecule, AP20187 (hereafter referred to as "AP" shown following) to dimerize FKBP-peptide fusions to create high affinity, bivalent ligands' that rapidly agonize specific targets. This process is schematically depicted in FIG. 1. See e.g., D. Varma, et al., 2010, *Proc Natl Acad Sci USA* 107:3493.

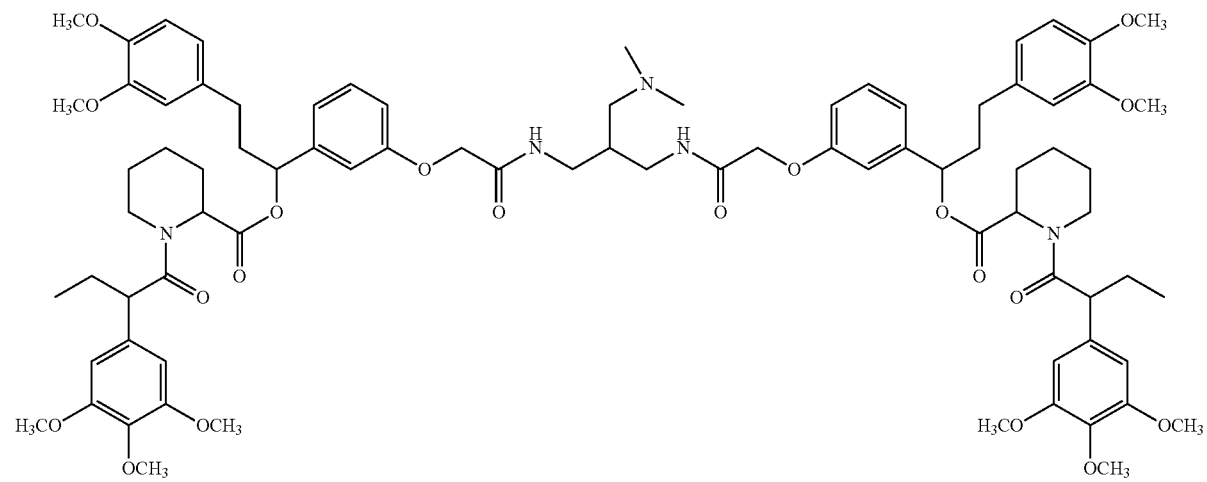

AP20187

We demonstrated that the expression and subsequent dimerization of a dynein light chain LC8 or TcTex1 molecular trap immediately affects dynein-associated processes (e.g., endosome, lysosome and Golgi dispersion). However, we could not easily remove the chemical dimerizer, AP, and thus could not reverse the perturbation to the system and follow its return to equilibrium. The ability to reverse this perturbation would provide additional, powerful insight to molecular processes that is not available with current technologies (e.g., siRNA, expression of a dominant negative construct, or functionality as part of this molecular trapping technology).

Example 1

Synthesis and Characterization of PhAP

Experimental Section
Synthesis of PhAP.

To a stirred solution of diol (9.5 mg, 0.045 mmol, 1 equiv) in $CH_2Cl_2$ (2 mL) were added acid (70 mg, 0.1 mmol, 2.2 equiv), cat. DMAP and DCC (24 mg, 0.12 mmol, 2.6 equiv) at rt. After 20 h, the solid was removed through filtration and the filtrate was concentrated in vacuum. The residue was purified by silica gel column chromatography (40-60% EtOAc/Hex) to afford the product (70 mg, 70%). HRMS $C_{86}H_{103}N_3O_{24}$ $[M+Na]^+$ calc'd 1584.6824, found. 1584.6830.

Construction of Expression Plasmids.

Both the LC8 and the FKBP-LC8$_{TRAP}$ were cloned in bacterial expression vector (pET21D), expressed and purified as described previously. See e.g., J. C. Williams, et al., 2007, *Proc Natl Acad Sci USA* 104:10028; D. Varma, et al., 2010, *Proc Natl Acad Sci USA* 107:3493. For GFP-tagged FKBP-LC8$_{TRAP}$, the construct was cloned as a C-terminal fusion of 'Enhanced green fluorescence protein (EGFP)' mammalian expression vector (pEGFPC1; Clontech) as described previously. See e.g., Varma et al., 2010, (Id.)

Native PAGE.

Each of, LC8 and FKBP-LC8$_{TRAP}$, were mixed in a molar concentration of 50 μM and 1.2 molar excess (60 μM) of AP20187 or 2.4 molar excess (120 μM) of PhAP20187. The mix were incubated at 4° C. for 5 min. Native PAGE analysis was performed at 16° C. using 8-25% gradient gels on the PHASTSYSTEM™ (GE Biosciences).

Antibodies and Reagents.

Anti-EEA1 monoclonal antibody was purchased from BD Biosciences, rhodamine-conjugated donkey anti-mouse secondary antibody from Millipore, mounting media PERMOUNT™ from Fisher Scientific, 37% formaldehyde from Sigma, LIPOFECTAMINE™ 2000 from Invitrogen, and OPTI-MEM™ media from GIBCO®, DMEM media from CELLGRO® and 10×PBS from CELLGRO®.

Cell Culture.

COS1 cells were cultured in DMEM (CELLGRO®) supplemented with 10% fetal bovine/calf serum (Omega Scientific). Transfection was performed in 80-90% confluent 24-h cultures of COS1 cells using LIPOFECTAMINE™ 2000 (Invitrogen) and OPTI-MEM™ media (GIBCO®) according to the manufacturer's recommendations. Various concentrations (0 nM to 1000 nM) of AP (Ariad Pharmaceuticals Inc.) and PhAP (as described herein) were added to each experimental wells 24 hr. post transfection and incubated for different periods of time before analyzing the cells. For reversibility of endosome dispersion studies, 500 nM of AP/PhAP were used. In each case, the cells were washed well with PBS and supplemented with fresh media before inducing with UV light (10 mins., 4 W, 350 nm) and allowed to recover for various time period at 37° C., before analysis.

Immunostaining and Microscopy.

For immunostaining, transiently transfected COS1 cells were fixed with 3.7% formaldehyde at room temperature for 10 min, and subsequent immunostaining was performed as described previously[2]. Briefly, COS 1 cells grown on 25-mm coverslips were washed 3× with PBS, treated with 3.7% formaldehyde (Sigma) in PBS for fixation, and permeabilized in 0.5% Triton X-100 (Sigma) in PBS at room temperature for 10 min. Cells were then incubated with blocking buffer containing 4% skimmed milk (fat free) and 0.5% Triton X-100 in PBS. Anti-EEA1 monoclonal antibody was added to label early endosome marker protein at a dilution of 1:100 in the same buffer for 30 min at RT, and the coverslips were washed and incubated with rhodamine-conjugated donkey anti-mouse secondary antibody (1:100). After washing, the coverslips were mounted on slides to visualize the trapping effects. Samples were viewed using an Olympus IX81 automated inverted microscope equipped with water immersion 60× objective. The level of dispersion was quantified by counting 100 cells per coverslip. Each experiment was performed in triplicate. Images were obtained using a Spot RT Slider high-resolution cooled CCD camera equipped to IX81 microscope and Image-Pro software. Images were cropped and processed using Adobe Photoshop 7.0 (Adobe Systems).

UV Induction.

For UV-induction and recovery of endosome studies, cells were washed with PBS and fresh media were added after drug treatment. The washed cells were then treated with a hand held UV-lamp (365 nm/4 watt) for 10 mins. The cells were then left to recover at 37° C. for varying period of time before staining and analysis.

Results and Discussion

First, we synthesized a UV-induced photolysable AP, by replacing the amine linker of AP with a photocleavable o-nitrobenzyl moiety to create PhAP (Scheme 1 following). This synthesis relied on the use of intermediate 5, which was prepared as described previously. See e.g., W. Yang, et al., 2000, *J Med Chem* 43, 1135. The final coupling between acid 5 and diol 6 produced the photocleavable modulator PhAP 1 with good yield. See e.g., A. M. Piggott & P. Karuso, 2005, *Molecules* 10:1292.

Scheme 1. Synthesis of PhAP (Cmpd 1)

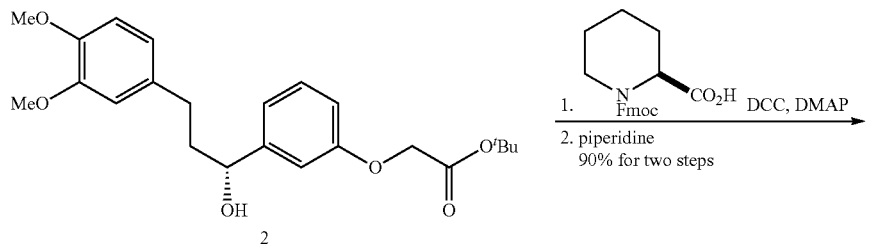

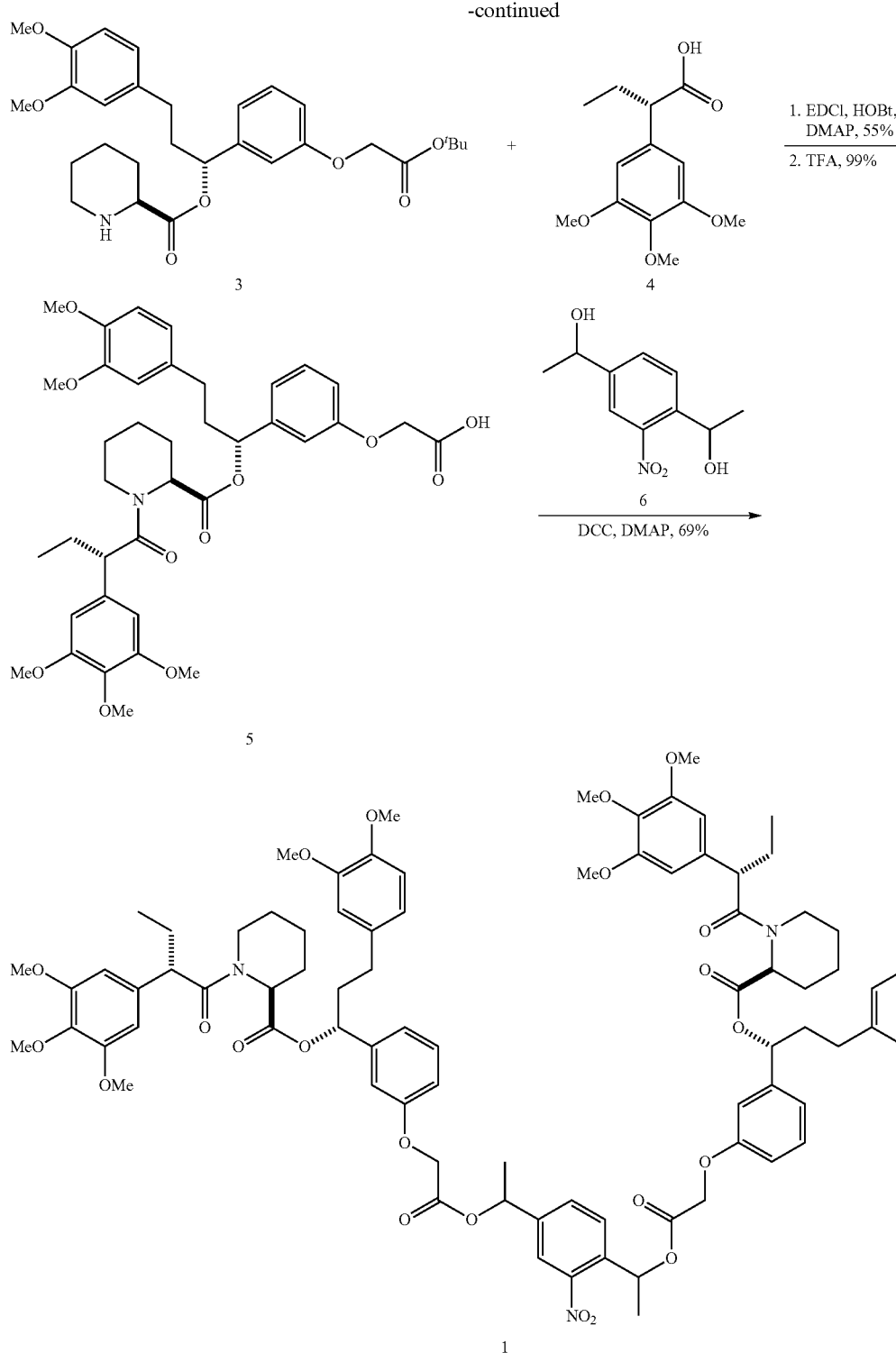

Figure 5:
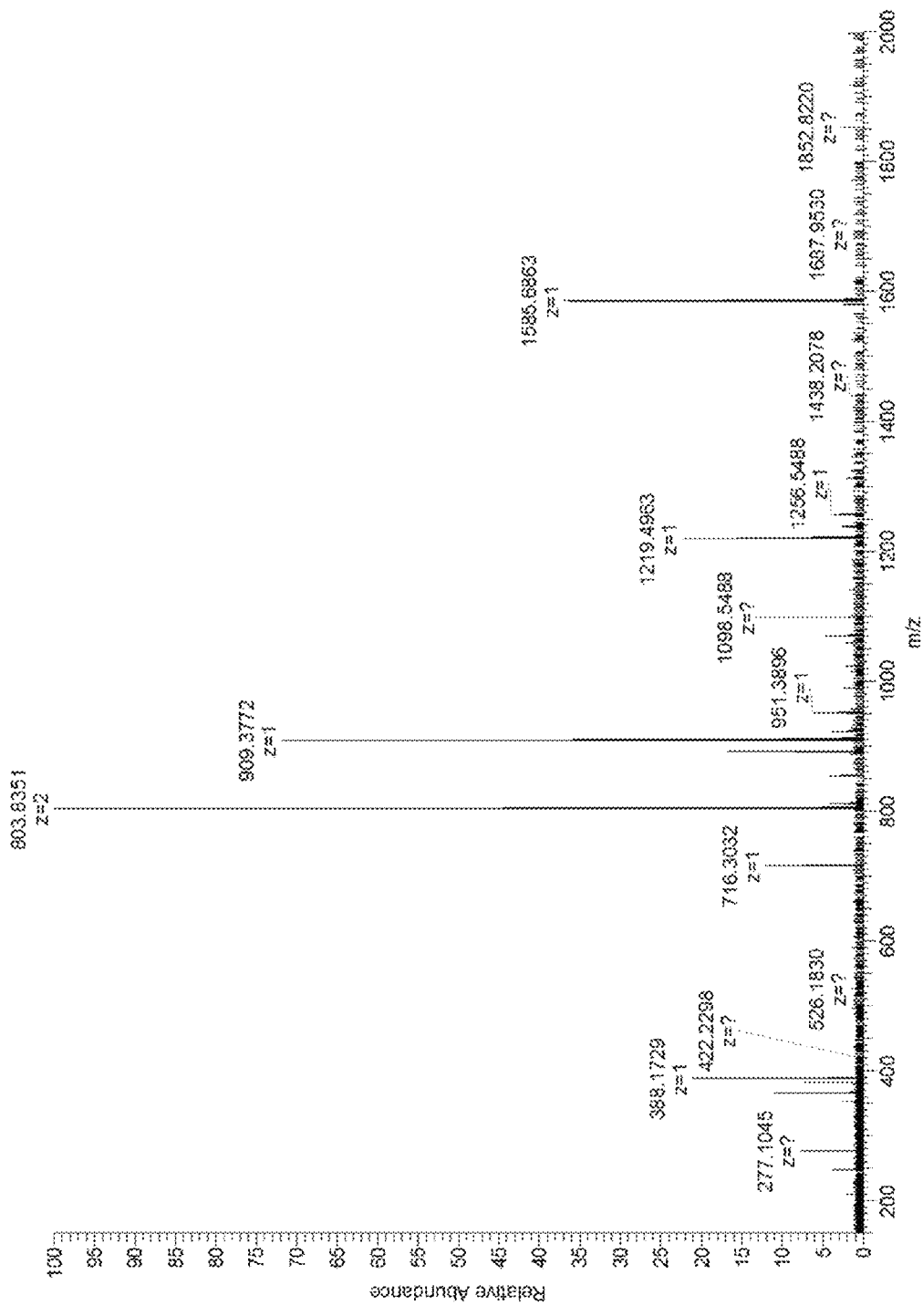
FIG. 5 depicts the mass spectrometry (MS) of the final product (PhAP) with molecular mass of 1585.6863 (exact mass—1584.6824).
Figure 6:
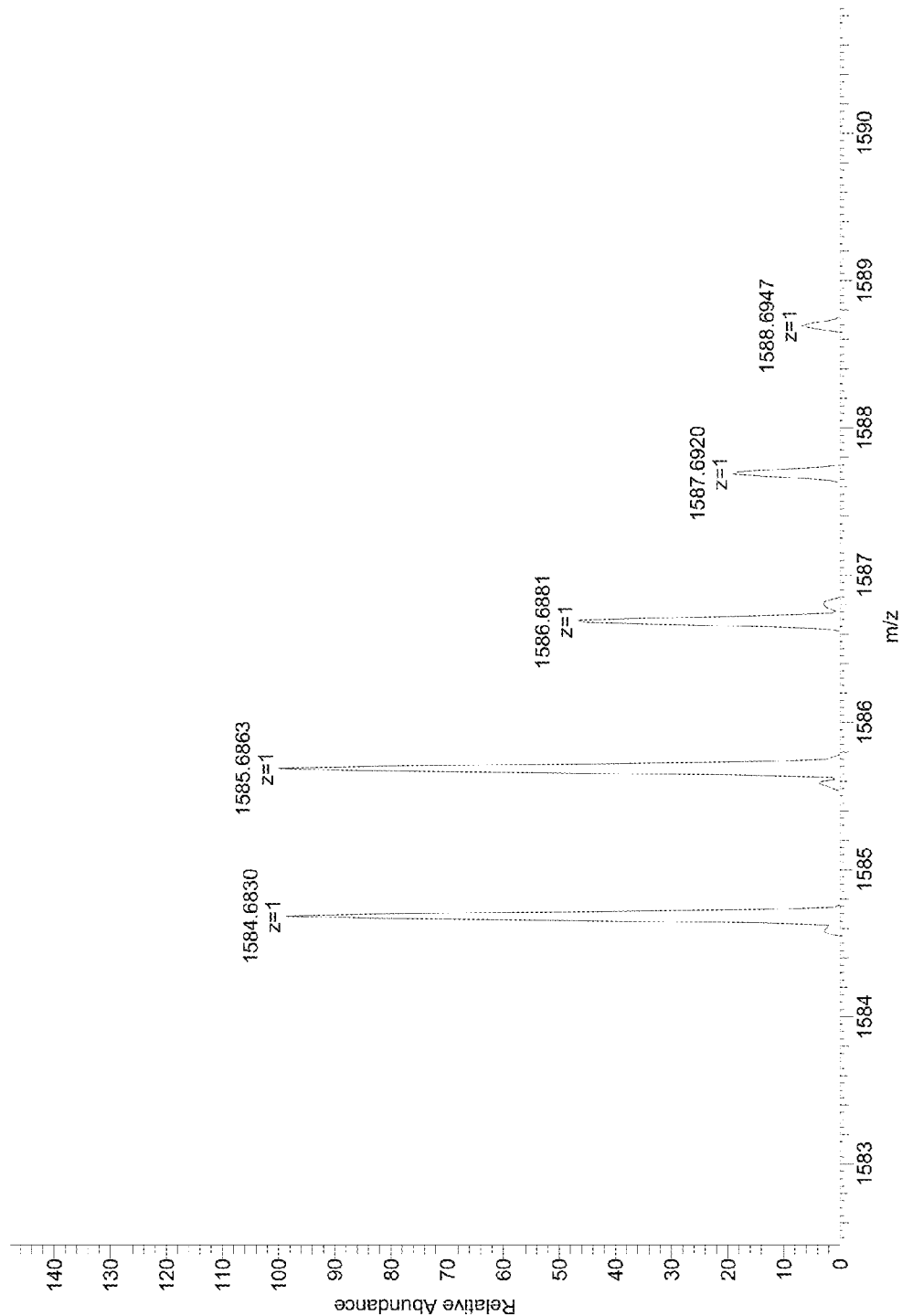
FIG. 6 depicts enlarged view of the MS data showing relative abundance of the final product (PhAP) (exact mass—1584.6824).
Figure 7:
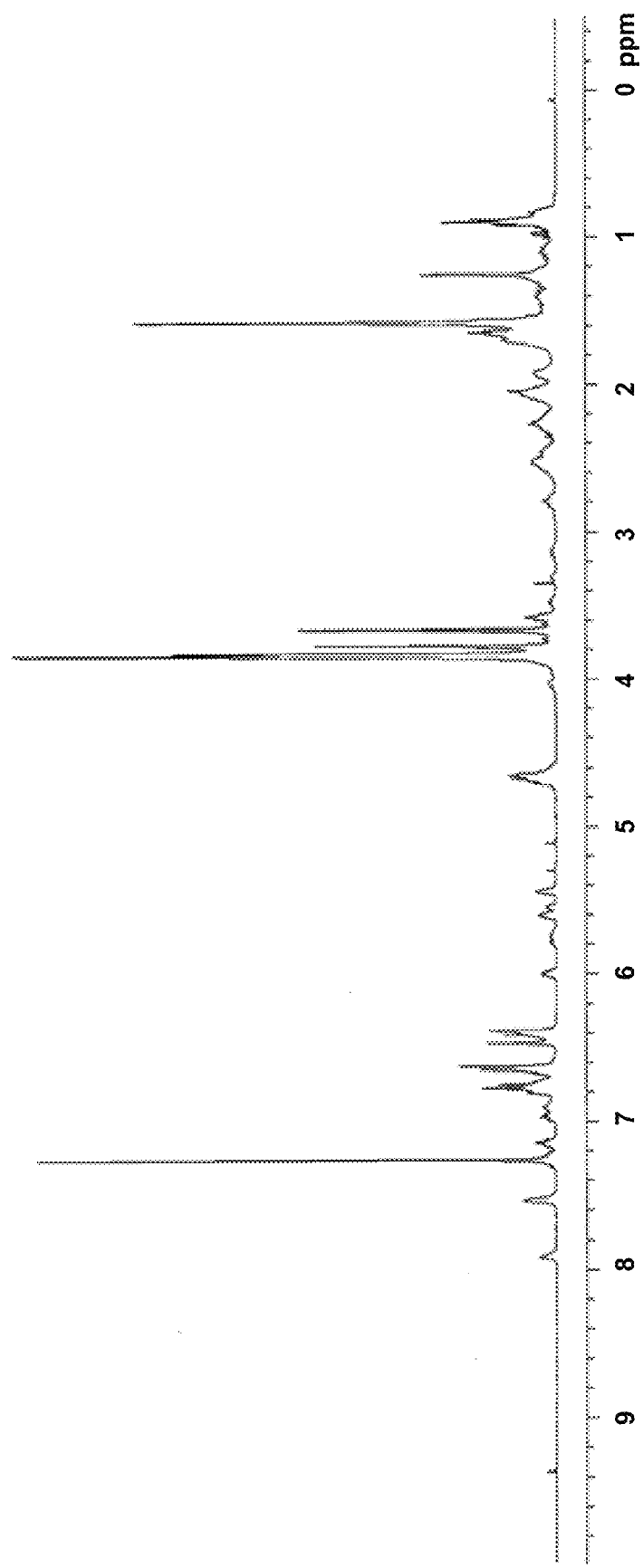
FIG. 7 depicts the NMR spectrum of PhAP.

Chemical structures of intermediates and products, and masses as determined by mass spectrometry are provided in FIGS. 4A-4I. The mass spectrum of PhAP is depicted in FIG. 5, having measured molecular mass of 1585.6863 Dalton (exact mass 1584.6824 Dalton). An enlarged view of the MS data showing relative abundance of the final product PhAP is provided in FIG. 6. The NMR spectrum at 400 MHz of PhAP is provided in FIG. 7. Conditions: Solvent $CDCl_3$; T=25.0 C.

We then tested whether this replacement of the amine linker with the o-nitrobenzyl moiety affected the dimerization of FKBP in vitro. We used native PAGE to follow the formation of the LC8-LC8 molecular trap ($LC8_{TRAP}$) complex induced by addition of PhAP. See e.g., Varma et al., 2010 (Id.) Upon the addition of PhAP to an equimolar mixture of LC8 and $LC8_{TRAP}$, we observed a new band that migrated the same distance as the band produced by addition of AP (FIG.

Figures 2B, 2D:
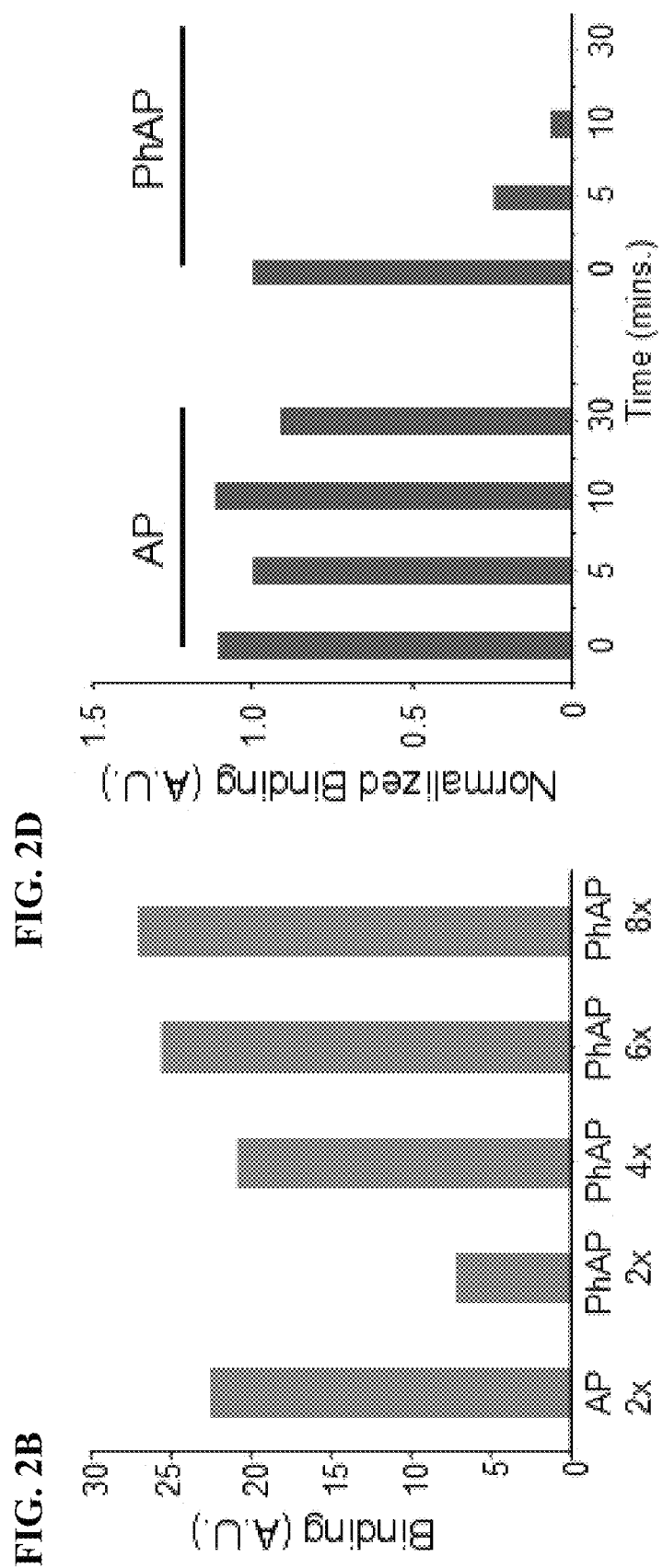
FIG. 2B: Quantification of the band intensities from A.
FIG. 2D) intensity ratio of the complex band versus the LC8 band as a function of UV exposure.

2A). Quantification of this new band indicated that a two-fold higher concentration (2×) of PhAP was required to produce a band of the same intensity as the band produced by the sample treated with AP (FIG. 2B).

Next, we characterized how well UV light could disrupt the PhAP-LC8-LC8$_{TRAP}$ complex in vitro. We generated the PhAP-LC8-LC8$_{TRAP}$ and AP-LC8-LC8$_{TRAP}$ complexes and exposed each to UV light (350 nm). Native PAGE indicated loss of the band corresponding to the PhAP-LC8-LC8$_{TRAP}$ complex and an increase in intensity of bands corresponding to the individual components after UV induction. The band corresponding to the PhAP-LC8-LC8$_{TRAP}$ complex was less intense in samples that received a five min exposure to UV light and undetectable after a 10 min exposure. On the other hand, the LC8-LC8$_{TRAP}$ complex induced by the non-photocleavable AP persisted, even after a 30 min exposure to UV light (FIG. 2C).

Figure 8A:
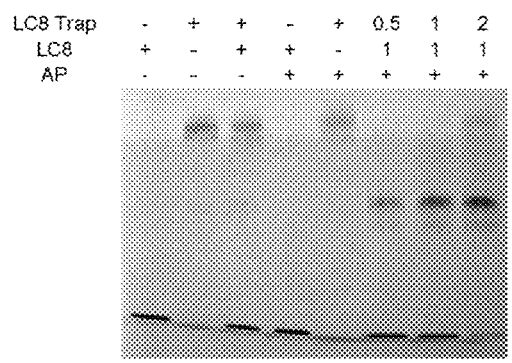
FIG. 8A depicts native PAGE analysis of stoichiometric complex formation between LC8 and FKBP-LC8$_{TRAP}$ on addition of dimerization agent AP. The admixture of LC8 and the LC8$_{TRAP}$ without the dimerization agent, AP, does not cause a shift in the LC8 band (lane 3). However, the addition of AP produces a new band that migrates midway down the gel (lanes 6-8).
Figure 8B:
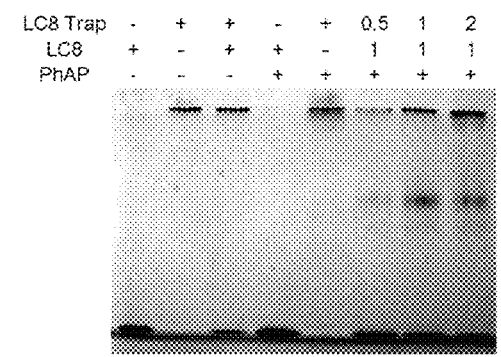
FIG. 8B depicts the results of the same experiment as FIG. 8A which was also conducted with PhAP to show that PhAP can also form complex between LC8 and FKBP-LC8$_{TRAP}$ efficiently.

Native PAGE analysis was conducted for stoichiometric complex formation between LC8 and FKBP-LC8$_{TRAP}$ on addition of dimerization agent AP. As depicted in FIG. 8A, admixture of LC8 and the LC8-LC8$_{TRAP}$ without the dimerization agent, AP, does not cause a shift in the LC8 band (lane 3). However, the addition of AP produces a new band that migrates midway down the gel (lanes 6-8). An analogous experiment employing PhAP was conducted, the results of which are depicted in FIG. 8B, which shows that that PhAP can also form complex between LC8 and FKBP-LC8$_{TRAP}$ efficiently.

To determine if these biochemical results had relevance in cells, we investigated if photocleavage of PhAP could reverse the endosome dispersion phenotype induced by LC8$_{TRAP}$ and AP. First, we established that PhAP behaved in a similar intracellular manner as AP. To this end, we used a green fluorescent protein (GPF) analog of the trap, EGFP-FKBP-LC8$_{TRAP}$ to identify cells that expressed the trap. COS1 cells were transiently transfected with EGFP-FKBP-LC8$_{TRAP}$ for 24 h, after which they were treated with PhAP or AP (0 nM-1000 nM) for 2 h. Cells were then fixed and stained with an early endosome marker 1 (EEA1). The number of cells with dispersed endosomes after treatment with PhAP or AP was indistinguishable. The maximum number of cells with dispersed endosomes (67.5±7.0% for PhAP and 64.1±7.6% for non-photocleavable AP), was obtained at dimerizer concentrations greater than 500 nM. The rate of dispersion was also similar using either dimerizing agent, and no changes were observed past 2 hours. The values obtained for both AP and PhAP are also in agreement with our previous studies. See e.g., Varma et al., 2010 (Id.)

Figure 9A:
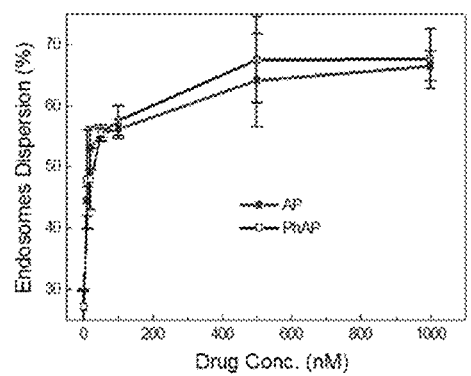
FIG. 9A: EGFP-FKBP-LC8$_{TRAP}$ transfected COS1 cells were treated with different concentration of the dimerization agent AP20187 (AP) or with the photolysable dimerization agent (PhAP) for 2 hrs. Cells were then fixed and stained for early endosome marker 1 (EEA1). In each case 100 cells were counted for endosomes dispersion and plotted as a function of concentration of AP/PhAP. Both AP and PhAP showed same effect on endosome dispersion as a function of concentration. Maximum dispersion is seen with 500 nM of drug concentration and remains unchanged with further increase in drug concentration. Each experiment was repeated in triplicate.

As depicted in FIG. 9A, EGFP-FKBP-LC8$_{TRAP}$ transfected COS1 cells were treated with different concentrations of the dimerization agent AP20187 (AP) or with the photolysable dimerization agent (PhAP) for 2 hrs. Cells were then fixed and stained for early endosome marker 1 (EEA1). In each case 100 cells were counted for endosomes dispersion and plotted as function of concentration of AP/PhAP. Both AP and PhAP showed same effect on endosome dispersion as a function of concentration. Maximum dispersion is seen with 500 nM of drug concentration and remains unchanged with further increase in drug concentration. Each experiment was repeated in triplicate.

Figure 9B:
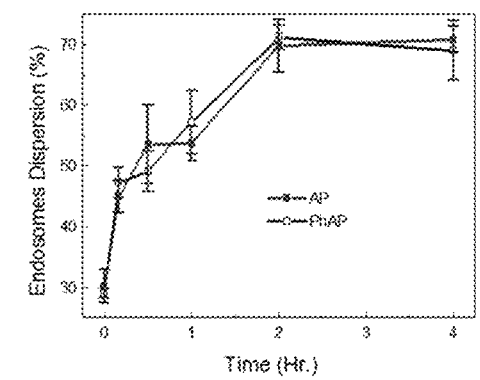
FIG. 9B: EGFP-FKBP-LC8$_{TRAP}$ transfected COS1 cells were treated with 500 nM of the dimerization agent AP20187 (AP) or with the photolysable dimerization agent (PhAP) for different times. Cells were then fixed and stained for early endosome marker (EEA1). In each case, 100 cells were counted to determine the extent of endosome dispersion and plotted as a function of time. Both AP and PhAP showed the same time dependence on endosome dispersion. Maximum dispersion was reached after 2 hr. of drug treatment and remains unchanged with further increase in time. Each experiment was repeated in triplicate (n=3).

As depicted in FIG. 9B, EGFP-FKBP-LC8$_{TRAP}$ transfected COS1 cells were treated with 500 nM of the dimerization agent AP20187 (AP) or with the photolysable dimerization agent (PhAP) for different times. Cells were then fixed and stained for early endosome marker (EEA1). In each case, 100 cells were counted to determine the extent of endosome dispersion and plotted as a function of time. Both AP and PhAP showed same time dependence on endosome dispersion. Maximum dispersion was reached after 2 hr. of drug treatment and remains unchanged with further increase in time. Each experiment was repeated in triplicate (n=3).

Figure 3A:
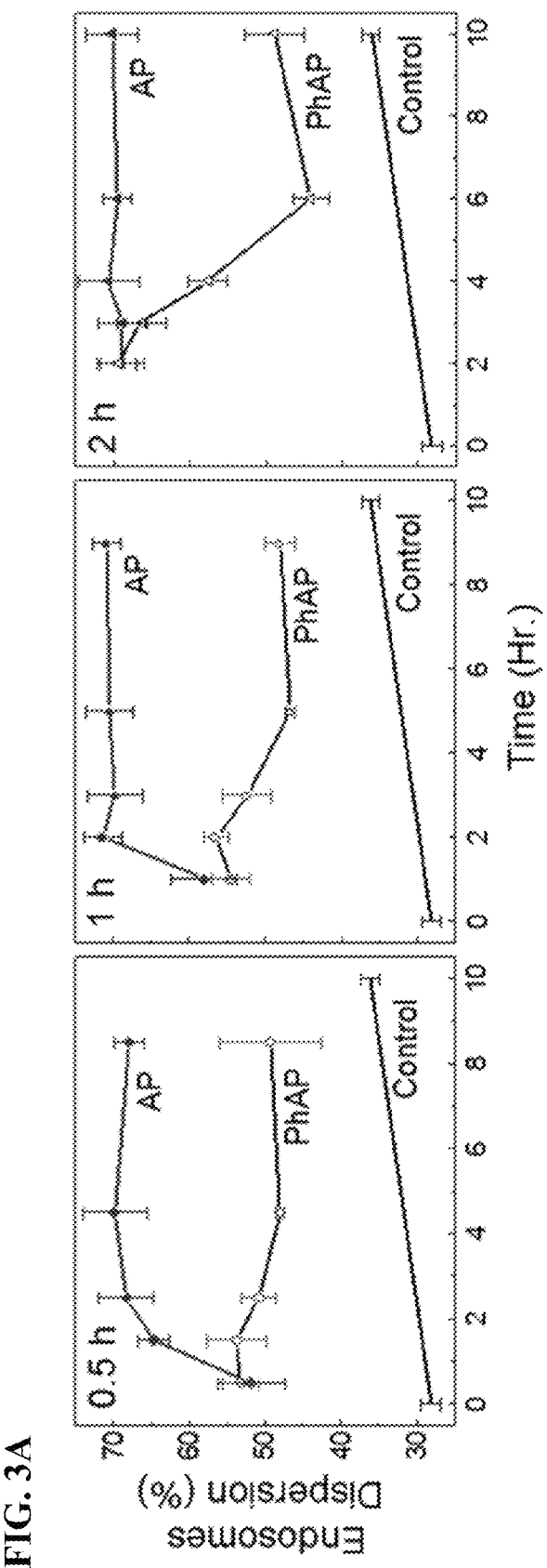
FIGS. 3A-3B depict cell-based assays and quantification.
Figure 3B:
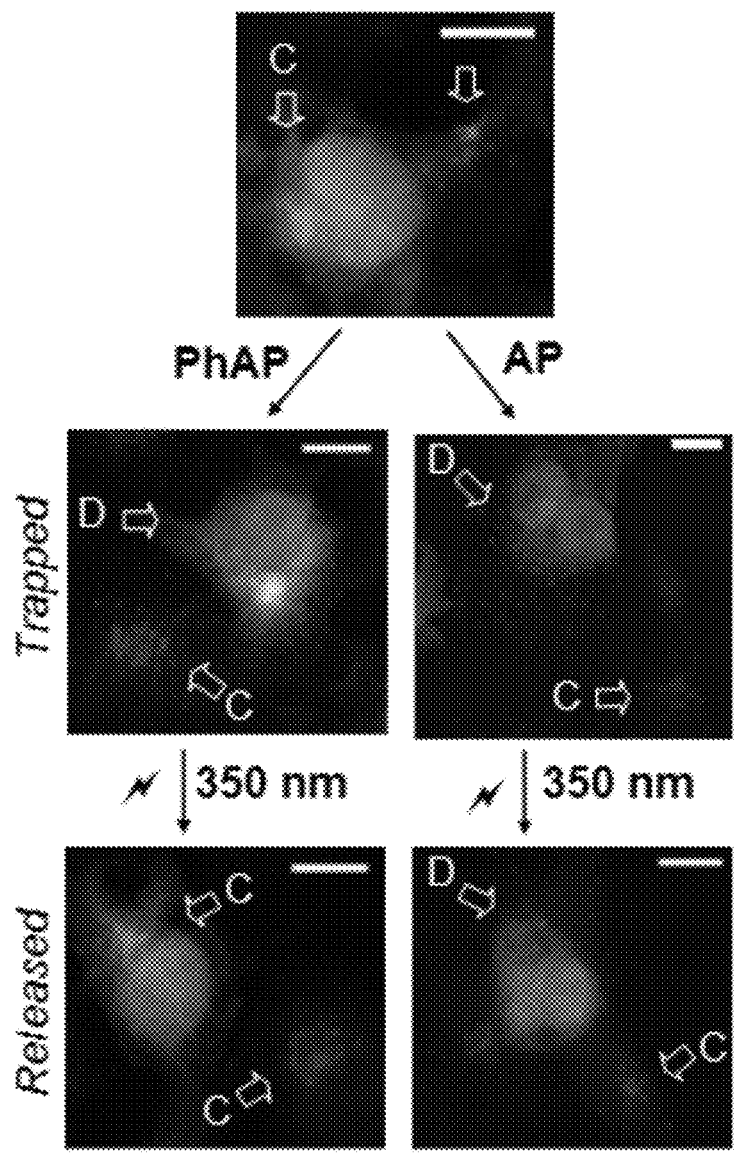
Figure 4A:
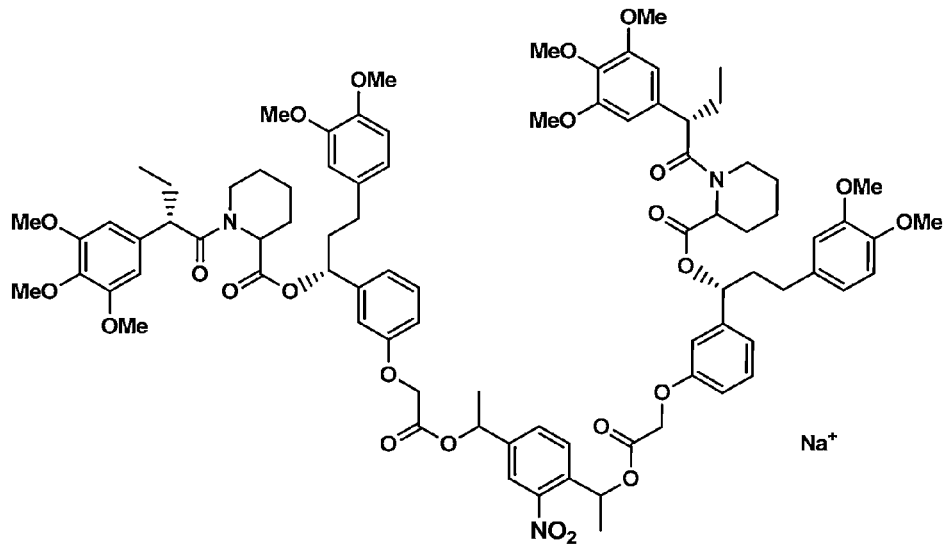
FIGS. 4A-4I depict the chemical structures, chemical formulae, and masses (m/z) as determined by mass spectrometry for compounds disclosed herein, intermediates, and final products in the synthesis of PhAP.
Figure 4B:
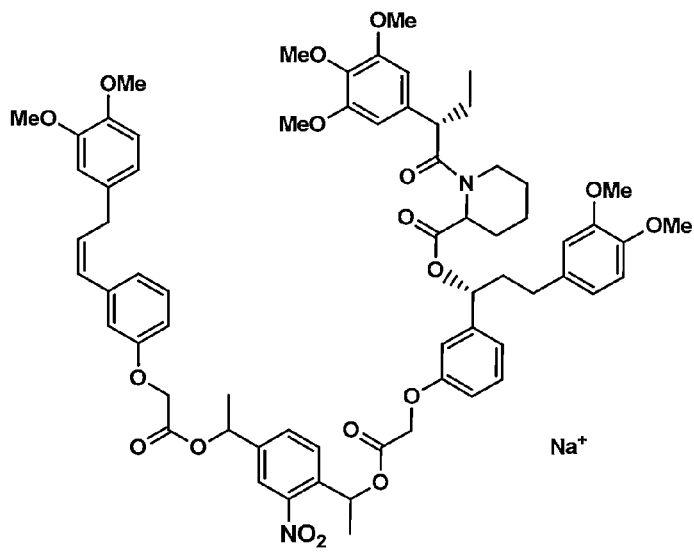
Figure 4C:
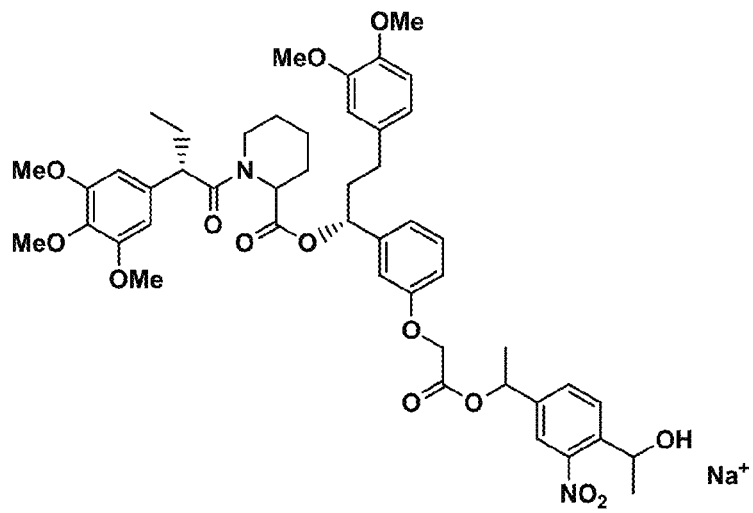
Figure 4D:
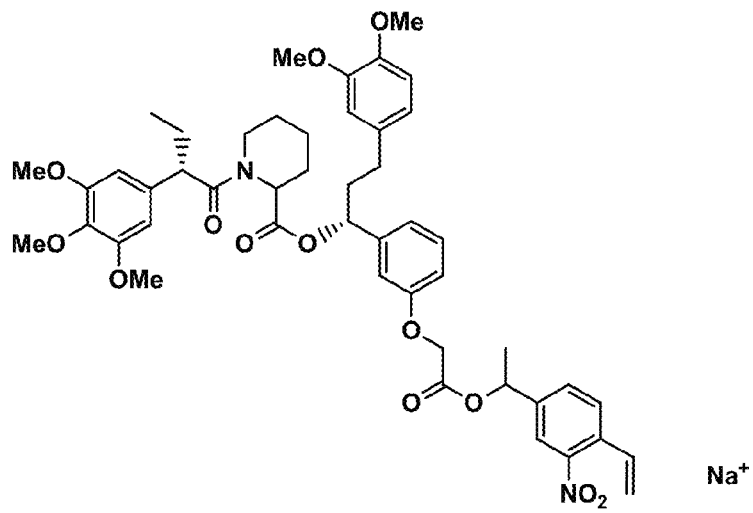
Figure 4E:
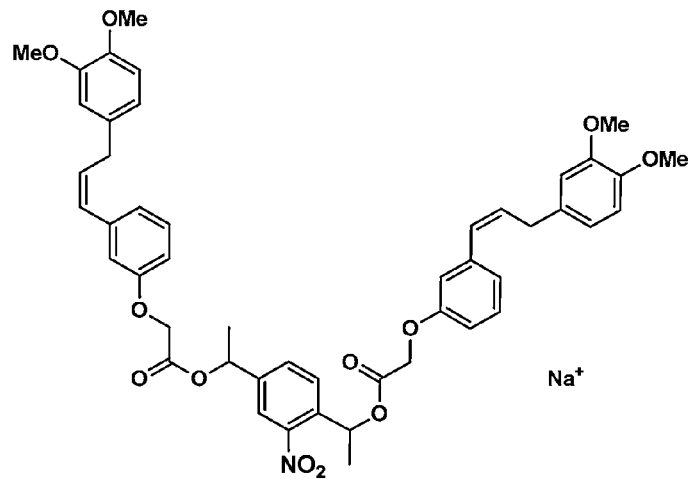
Figure 4F:
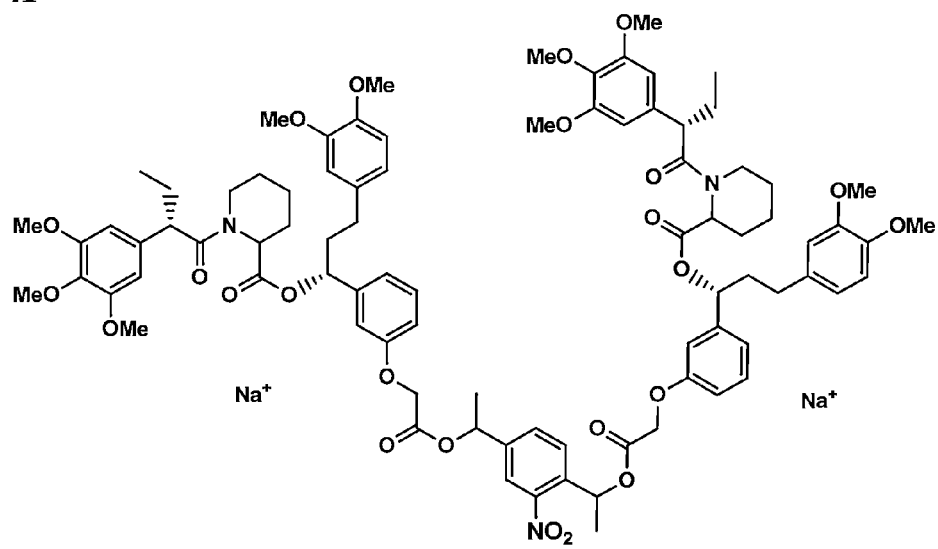
Figure 4G:
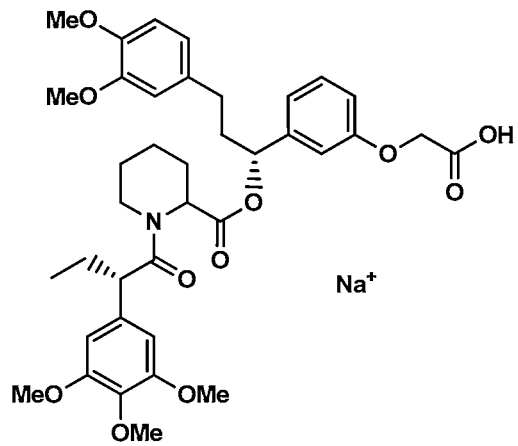
Figure 4H:
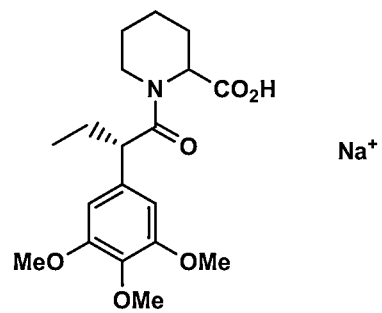
Figure 4I:
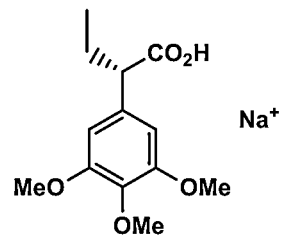

Next, we characterized the reversibility of endosome dispersion in COS1 cells UV-induced cleavage of PhAP. In these experiments, transiently transfected cells were incubated with PhAP (500 nM) or AP for times ranging from 0-2 h, after which cells were washed rapidly, replenished with fresh media, and then exposed to UV light (10 min, 4 W, 350 nm). The cells were then fixed at 0, 1, 2, 4, and 8 h post UV radiation and the endosomes imaged using fluorescence microscopy at 60× magnification. We observed a gradual recovery of endosomes to the perinuclear region during the first 4 h after UV exposure (44.1±2.3%), with a slight increase in dispersion after 8 h (48.9±3.9%), for cells treated with PhAP (FIG. 3A). On the other hand, when cells were treated with AP, the endosomes remained dispersed at all time points evaluated, regardless of whether they received UV exposure. As an additional control, cells that were not transfected (i.e., did not express GFP) were treated in the same manner. These cells showed a slight increase in endosome dispersion in the 8 h after UV exposure.

The results of the effect of drug concentration (i.e., AP or PhAP) on endosome dispersion are tabulated in Table 1 following.

TABLE 1

Percentage of endosomes dispersion as a function of AP/PhAP concentration after 2 hr. of treatment.

| Drug Conc. (nM) | AP (%) | PhAP (%) |
|---|---|---|
| 0 | 26.9 ± 3.1 | 27.2 ± 2.5 |
| 10 | 44.4 ± 2.4 | 47.9 ± 8.1 |
| 20 | 53.0 ± 3.5 | 48.0 ± 5.0 |
| 50 | 55-5 ± 0.7 | 55.5 ± 1.3 |
| 100 | 56.2 ± 1.6 | 57.5 ± 2.4 |
| 500 | 64.1 ± 7.6 | 67.5 ± 7.0 |
| 1000 | 66.4 ± 2.5 | 67.7 ± 4.9 |

The time course of the effect of drug (i.e., AP or PhAP at 500 nM) on endosome dispersion are tabulated in Table 2 following.

TABLE 2

Percentage of endosomes dispersion as a function of time with 500 nM of AP/PhAP concentration.

| Time (Hr) | AP (%) | PhAP (%) |
|---|---|---|
| 0 | 30.2 ± 2.8 | 29.0 ± .8 |
| 0.167 (10 min.) | 45.0 ± 2.6 | 47.2 ± 2.5 |
| 0.5 | 53.6 ± 6.5 | 49.1 ± 3.3 |
| 1 | 53.8 ± 2.9 | 57.2 ± 5.2 |
| 2 | 69.8 ± 4.3 | 71.2 ± 2.0 |
| 4 | 70.9 ± 2.1 | 69.0 ± 4.9 |

The percentage of endosomes dispersion at different time point (showing recovery for PhAP), after 2 hr. of AP/PhAP treatment (500 nM) are tabulated in Table 3 following.

TABLE 3

Percentage of endosomes dispersion at different time point (showing recovery for PhAP), after 2 hr. of AP/PhAP treatment (500 nM).

| Recovery after 2 Hr Drug Treatment | AP (%) | PhAP (%) |
|---|---|---|
| 0 | 69.1 ± 3.2 | 69.5 ± 2.4 |
| 1 | 68.9 ± 3.2 | 66.3 ± 3.2 |
| 2 | 70.7 ± 4.0 | 57.6 ± 2.6 |
| 4 | 69.5 ± 1.9 | 44.1 ± 2.3 |
| 8 | 70.3 ± 3.3 | 48.9 ± 3.9 |

The percentage of endosomes dispersion at different time point (showing recovery for PhAP), after 1 hr. of AP/PhAP treatment (500 nM), are tabulated in Table 4 following.

TABLE 4

Percentage of endosomes dispersion at different time point (showing recovery for PhAP), after 1 hr. of AP/PhAP treatment (500 nM).

| Recovery after 1 Hr Drug Treatment | AP (%) | PhAP (%) |
|---|---|---|
| 0 | 58.0 ± 4.3 | 57.8 ± 8.0 |
| 1 | 71.2 ± 2.5 | 56.4 ± 1.7 |
| 2 | 69.7 ± 3.6 | 55.7 ± 8.8 |
| 4 | 70.4 ± 3.1 | 46.7 ± 0.6 |
| 8 | 70.8 ± 1.9 | 48.1 ± 2.0 |

The percentage of endosomes dispersion at different time point (showing recovery for PhAP), after 30 mins. of AP/PhAP treatment (500 nM), are tabulated in Table 5 following.

TABLE 5

Percentage of endosomes dispersion at different time point (showing recovery for PhAP), after 30 mins. of AP/PhAP treatment (500 nM).

| Recovery after 30 min Drug Treatment | AP (%) | PhAP (%) |
|---|---|---|
| 0 | 51.8 ± 4.4 | 53.2 ± 2.4 |
| 1 | 64.7 ± 2.0 | 53.7 ± 4.0 |
| 2 | 68.3 ± 3.7 | 50.8 ± 2.3 |
| 4 | 69.8 ± 4.3 | 48.0 ± 0.5 |
| 8 | 67.9 ± 1.9 | 49.3 ± 6.7 |

Of note, cells with compact endosomes 4 h after UV treatment did not return to the same percentage before the addition of PhAP. However, this is not entirely unexpected because we typically observe that 20-25% of cells have dispersed endosomes, including trap-bearing cells before the addition of PhAP or AP, as well as cells not transfected with the trap. We also observed that a maximum of 70-75% of cells transfected with the trap had dispersed endosomes after treatment with PhAP or AP for 2 h. We suspect that incomplete recovery arises from several sources, including cell heterogeneity (see e.g., R. J. Hastings & L. M. Franks, 1983, *Br J Cancer* 47:233), effects of transient transfection, and the fact that cells were not synchronized throughout the experiment. However, similar spreads in these values have been reported in cell-based assays that used different methods to interfere with dynein-mediated processes, including RNAi (see e.g., K. J. Palmer, et al., 2009, *Mol Biol Cell* 20:2885; R. Dixit, et al., *J Biol Chem* 2008, 283:33611), expression of a dominant-negative protein (see e.g., O. N. Zhapparova, et al., 2007, *Biochemistry* (Mosc) 72:1233) and/or microinjection of monoclonal antibodies (see e.g., A. F. Palazzo, et al., 2001, *Curr Biol* 11:1536; all of which are irreversible. Consistent with these results, in RNAi experiments targeting LC8, we observed that only 65% of cells showed dispersion of the Golgi after 4 days of treatment as compared to 12% of cells exposed to a scrambled control.

Having established that photocleavage of PhAP reverses the phenotype, we asked whether the amount of time needed to restore perinuclear clustering of endosomes depended on how long the trap was allowed to act. As mentioned above, we found that maximal endosome dispersion occurred within 2 h whereas the recovery occurred over a 4 hr period. Thus, we treated cells for 30 minutes and 1 hr with PhAP or AP followed by UV exposure. As expected, it resulted in a lower percentage of cells that had dispersed endosomes (0.5 h, 53.2±2.4%; 1 h, 57.8±8.0%). However, for all treatment times (0.5, 1, and 2 h), the percentages of cells with dispersed endosomes were similar within 4 h after exposure to UV light (FIG. 3A). In contrast, cells treated exactly the same, but with AP instead of PhAP, exhibited continued increases in endosome dispersion until dispersion reached the saturation point (~70%), further confirming that induction of the trap with AP creates a highly stable complex. Why the time needed for endosomes to return to the perinuclear space was similar despite the treatment-time-dependent differing percentages of cells with dispersed endosomes after PhAP treatment remains an open question. It is important to point out, however, that these values reflect changes averaged over a large number of cells and detailed mechanistic insight into this process will require live cell imaging (e.g., following endosome dispersion in individual cells before, during, and after cleavage of PhAP). Now that we have established the reversibility of the PhAP-mediated trap, such mechanistic studies are possible.

In summary, we have developed photocleavable analogs of AP, demonstrated that PhAP can induce formation of the LC8-LC8$_{TRAP}$ complex, and that photocleavage of PhAP within this molecular trap leads to dissociation and rapid reversal of endosome dispersion. Although we have applied this new reagent in the context of molecular trapping (see e.g., Varma et al., 2010, Id.), dimerization of FKBP can be used in many other systems, typically to induce a signal cascade (see e.g., S. A. Zlatic, et al., 2011, *Mol Biol Cell* 22:1699; D. J. Baker, et al., 2005, *Nature* 479:232; U. B. Pajvani, et al., 2005, *Nat Med* 11:797; S. Gazdoiu, et al., 2005, *Proc Natl Acad Sci USA* 102:15053; H. Abdel-Azim, et al., 2008, *Blood* 111:4064), or to oligomerize amyloid precursor protein (see e.g., H. Abdel-Azim, et al., 2008, Id.; M. Beland, et al., 2012, *J Neurosci* 32:13255; A. Roostaee, et al., 2009, *J Biol Chem* 284:30907), or as a 'death switch' for cell-based therapies (see e.g., A. Di Stasi, et al., 2011, *N Engl J Med* 365:1673), or the like. PhAP will be of value to these studies as well. Finally, we note that a photocleavable rapamycin analog was recently created to dimerize FKBP and FRAP. In this case, the photocleavage was used to activate the rapamycin analog for spatial and temporal activation of the signaling event. See e.g., N. Umeda, et al., 2011, *J Am Chem Soc* 133:12; R. DeRose, et al., 2012, *J Vis Exp* 2012. PhAP presented herein, in conjunction with a molecular trap expressed by a tissue specific promoter, not only affords spatial and temporal activation of a biological process in an animal model (e.g., *C. elegans*), but also the ability to reverse a phenotype.

Example 2

Development of LC and IC Traps

Introduction

We wish to understand the role of the dynein LCs in cargo recruitment and regulation of dynein activity. Originally, the dynein light chains were hypothesized to anchor cargo to the dynein motor complex. In time, this adaptor hypothesis become pervasive, and reports identifying a novel interaction between the protein of interest and a dynein LC invariably assumed the function of this interaction was for retrograde transport. Specifically, the structure of the LCs (LC8 [Dynll1] and TcTex1 [Dynlt1]) bound to the dynein IC indicate that the dynein IC occupies the same site as putative cargo. Moreover, the LCs are homodimeric and contain two symmetric binding sites. Yet, in the structure of the IC-LC8-TcTex1 complex, both binding sites on each LC are occupied by the dynein IC, thereby preventing the LCs from binding putative cargo. Finally, the dynein IC, within the context of the dynein complex, is dimeric, as are most of the characterized LC-interacting proteins (e.g., nNOS). This dimeric organization of the LCs and their targets gives rise to a bivalent-bivalent interaction, which is generally of higher affinity, due to energy additivity, than a tripartite interaction (e.g., target-LC-IC)12.

While it is unlikely that the LCs directly participate in bridging cargo to the dynein motor complex, recent investigations suggest the LCs may regulate specific functions of dynein, such as the dynein-dynactin interaction and/or phosphorylation of the IC. In particular, the dynein LCs can bind regions within proteins that are predicted to be intrinsically disordered, and recent studies in various systems have implicated such intrinsically disordered regions as frequently participating in the regulation of protein activity and/or function. In addition, evidence of a dynein-independent role of the LCs is beginning to emerge. LC8 has been implicated in regulating the activity of TRPS145 and nNOS46. Recent studies have also shown that LC8 participates in nuclear import of the Rabies P protein and 53BP1. Furthermore, we recently showed in MCF-7 cells and zebrafish that LC8 is necessary for nuclear import of Pak1. Because the LCs are essential for dynein function and also appear to have multiple dynein-independent roles it is difficult to address their specific cellular functions. Therefore, we initially developed inducible molecular traps to begin to address the potential role of the LCs as allosteric regulators of their target.

Initial Studies.

Figure 10A:
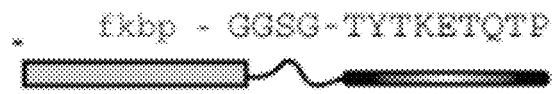
FIGS. 10A-10E depict the biochemical characterization of the LC traps disclosed in Example 2.
Figure 10B:
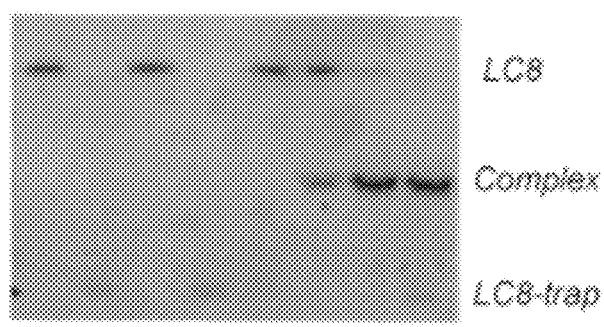
Figure 10C:
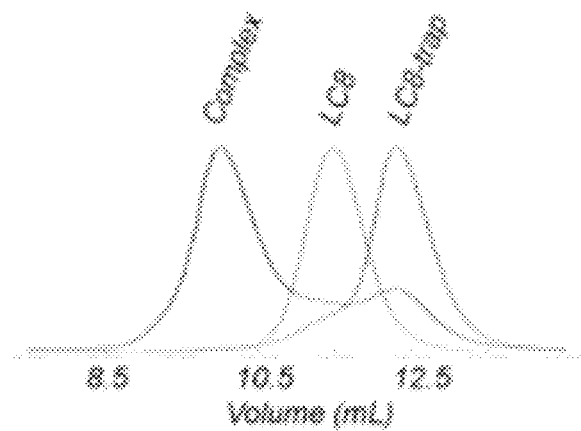

We fused the LC8 binding region of the dynein IC (REIV-TYTKETQTP; residues 125-137; rat IC2C numbering) (SEQ ID NO:5) to the C-terminus of FKBP (FIG. 10A). Because the intended function of this construct is to sequester LC8 in vivo, we refer to this construct as an "LC8-trap." The LC8-trap and LC8 were expressed in bacteria and purified to homogeneity using standard techniques. To test the relative affinity of monomeric vs. dimeric LC8-trap with LC8 we used native polyacrylamide gel electrophoresis (PAGE). The LC8-trap (isoelectric point=9.2) migrated toward the anode and was not visible, whereas LC8 (isoelectric point=7.4) migrated as a tight band toward the cathode, close to the dye front. In the presence of AP20187, the admixture of the LC8-trap and LC8 produced a new band, approximately midway down the gel (FIG. 10B), while the individual proteins were unaffected by the presence of AP20187. This interaction appeared to be stoichiometric, as judged by electrophoretic analysis of LC8 with increasing amounts of the LC8-trap (FIG. 2B). To verify the native PAGE experiments, we performed size exclusion chromatography (SEC). LC8 and the LC8-trap eluted at 11.5 mL and 12.1 mL, respectively, as individual species (FIG. 10C). However, when AP20187 was added to the mixture of LC8 and LC8-trap, we observed a shift to earlier elution volumes, 10.0 mL, and depletion of the individual components from the later elution volumes. SDS-PAGE of the fraction eluting at 10.0 mL indicated the presence of both components.

Figures 10D, 10E:
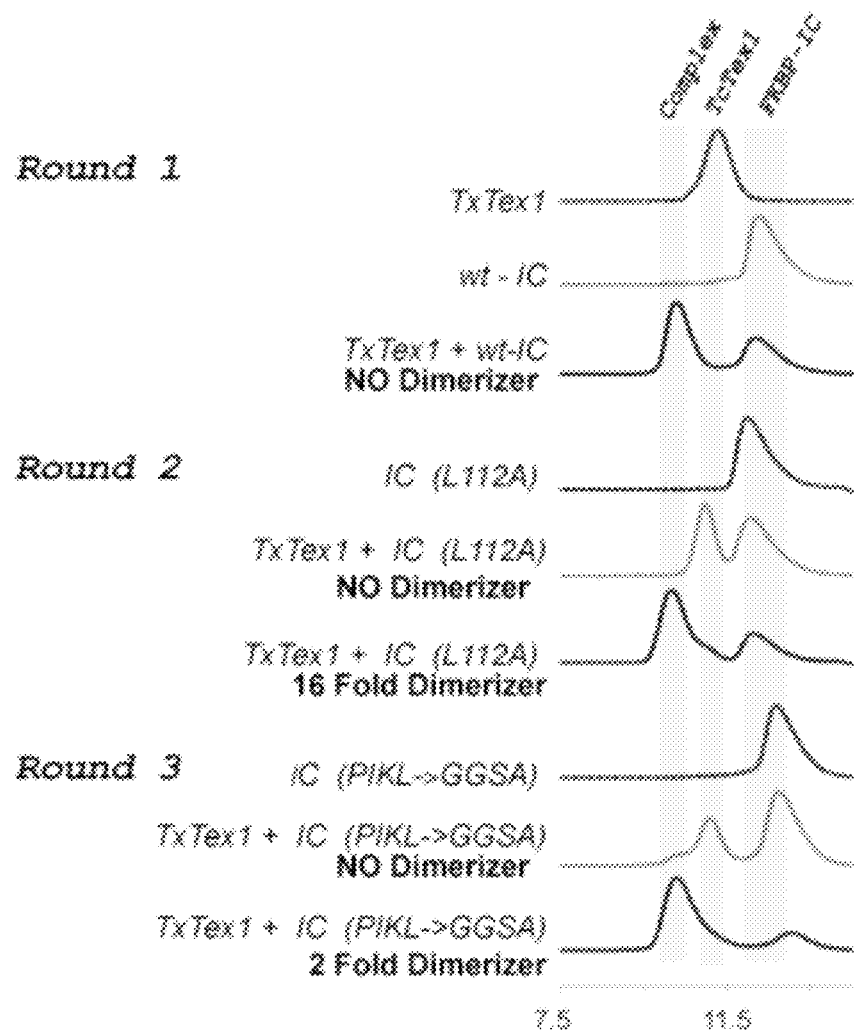

To generate a TcTex1 trap, residues 107-125 of rat dynein IC2C, which specifically interact with TcTex1, were fused to the C-terminus of FKBP (FKBP-IC; FIG. 10D). Native gel and SEC experiments of the admixture indicated FKBP-IC peptide bound to TcTex1 in the absence of AP20187, suggesting the interaction is of higher affinity than the IC-LC8 interaction (FIG. 10E round 1). To reduce the affinity of the monovalent interaction, we introduced the L112A point mutation, shown by us and others to significantly reduce the TcTex1 affinity. Admixtures of the mutated FKBP-IC (L112A) peptide and TcTex1 did not interact in the absence of AP20187, as judged by native PAGE and SEC (FIG. 10E, round 2). However, addition of AP20187 to the admixture of FKBP-IC (L112A) peptide and TcTex1 produced a shift, but required a 16-fold higher concentration of AP20187 than the LC8/LC8-trap interaction (FIG. 10E, round 2). Based on this observation, we hypothesized that the sequence immediately preceding the TcTex1-binding region may interfere with the interaction, either through conformational restriction due to P109 or electrostatic repulsion due to K111. Therefore, we mutated the sequence PIK to GGS, to introduce flexible, hydrophilic residues (residues 109-111) (FIG. 10D). The modified FKBP-IC trap fully sequestered TcTex1 at ~8-fold lower concentrations of AP20187 than the FKBP-IC (L112A) peptide, or approximately twice that required for the LC8-trap (FIG. 10E, round 3).

Although our previous structural studies showed that LC8 and TcTex1 bind to their targets in a similar manner and to adjacent sites on the dynein IC1, there are no known common binding partners that simultaneously bind LC8 and TcTex1 (other than the IC). In addition, there is no evidence that LC8 can bind proteins bearing a TcTex1 sequence or vice versa (e.g., LC8 binds to BimEL, Pak1, nNOS, etc.; TcTex1 binds to Doc2α, PTHR receptor, etc. 50). Nonetheless, based on their structural similarity, we were compelled to demonstrate that the traps were specific to their target. Native PAGE revealed that the LC8-trap does not bind to TcTex1, with or without AP20187 treatment, and that the TcTex1-trap does not bind to LC8 (data not shown).

Figure 11A:
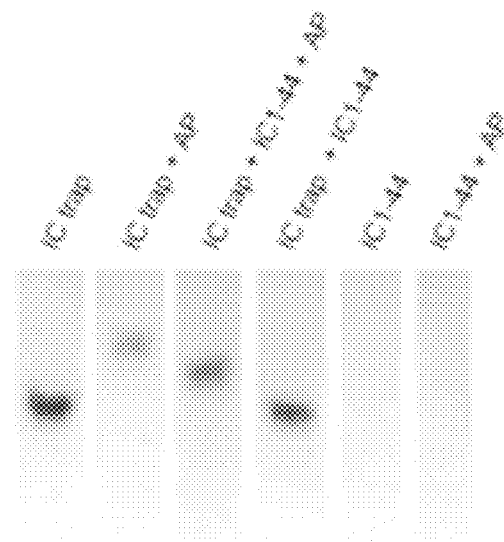
FIGS. 11A-11C depict biochemical characterization of an IC trap.
Figure 11B:
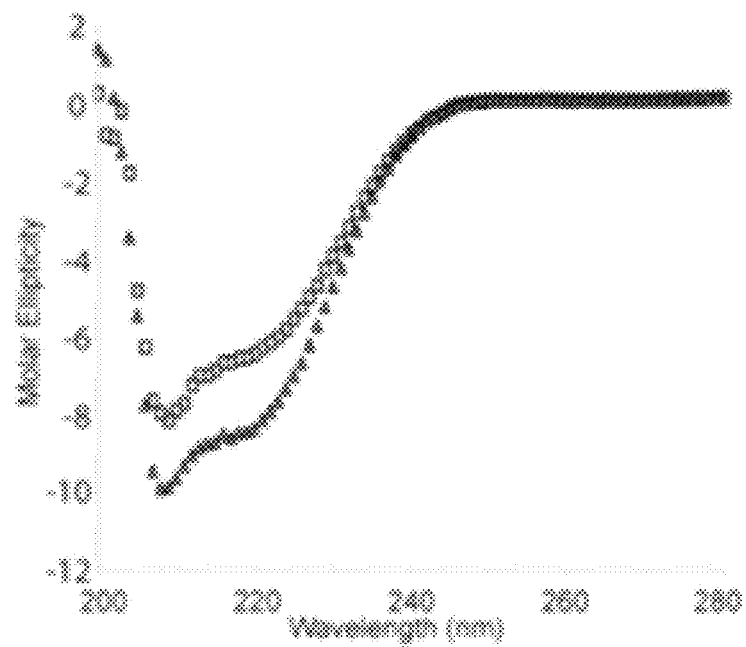
Figure 11C:
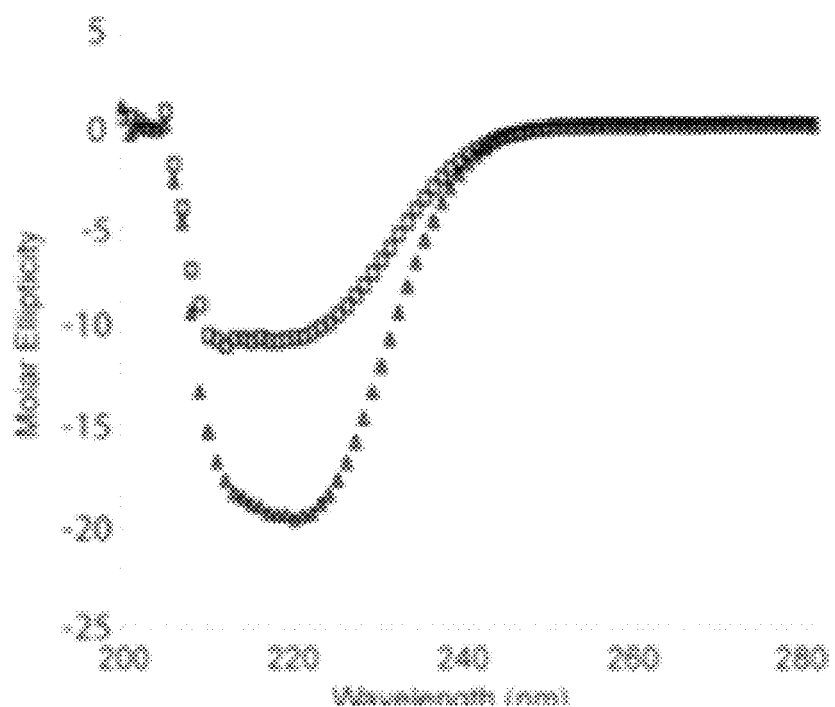

Finally, we designed an IC trap based on extensive biochemical and biophysical studies to map and characterized the dynein-dynactin interaction. Using various fragments of the dynein IC and p150Glued, we showed by size exclusion chromatography (SEC), native polyacrylamide gel electrophoresis IPAGE), analytical ultracentrifugation (AUC), circular dichroism (CD), and nuclear magnetic resonance (NMR) that a construct containing residues 381-530 of p150Glued comprise the dynein IC binding site. We also observed that this construct undergoes a dimer-to-monomer transition at 16+1° C. Finally, sedimentation equilibrium studies show the interaction between the dynein IC and dynactin p150glued fragment required dimerization of the p150glued fragment. Based on these results, we hypothesized that fusing the p150glued fragment to FKBP and using AP20187 to force its dimerization would permit IC binding at physiological temperatures (e.g., 37° C.). Native PAGE and CD studies confirmed this design (FIGS. 11A-11C). AUC studies at 25° C. also indicated that the IC trap binds the IC only in the presence of AP20187 (data not shown).

Taken together, these biochemical experiments represent a rational strategy to generate an inducible, high affinity trap to a specific target.

In Vivo Effect of Dynein LC and IC Traps.

Figures 12A, 12B, 12C:
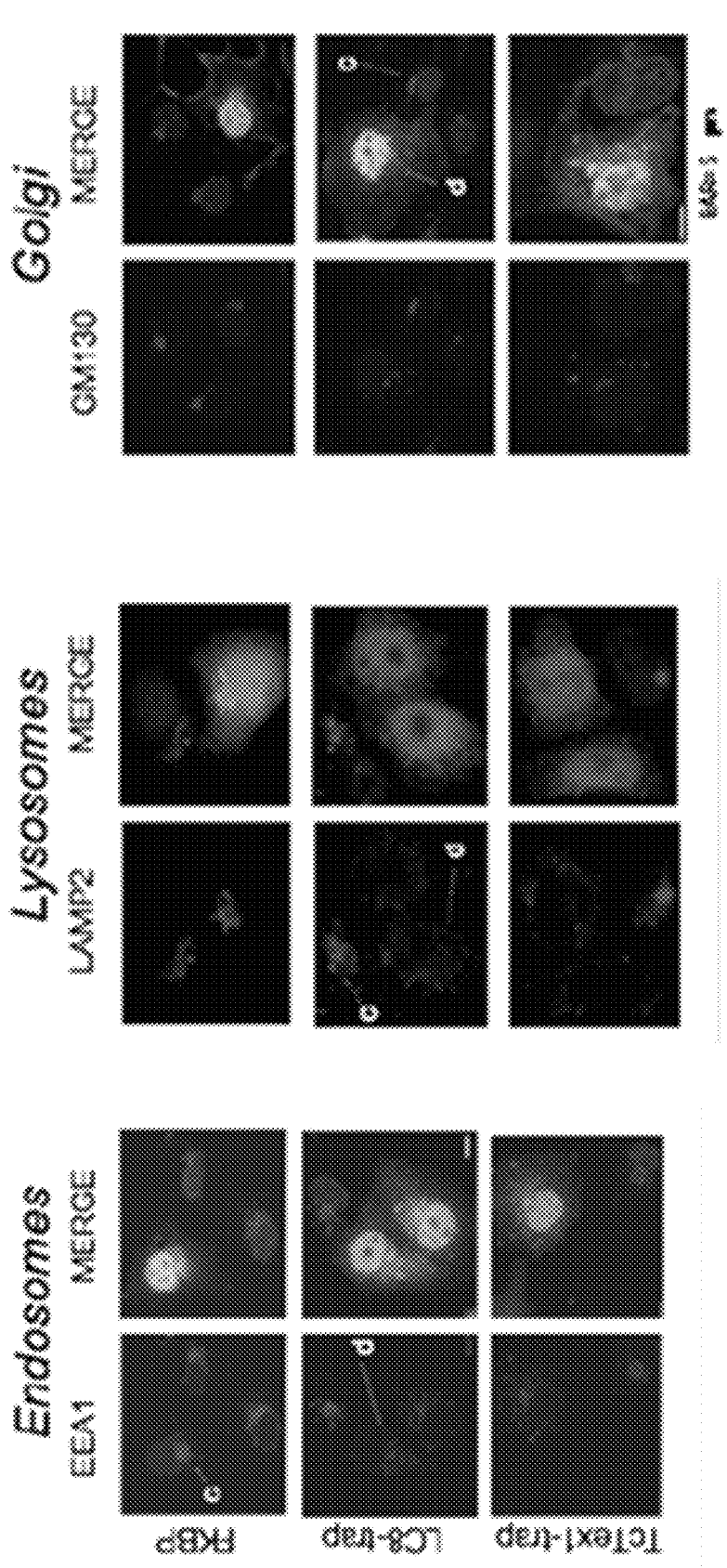
FIGS. 12A-12C depict induction of LC traps which leads to endosome, lysosome and Golgi apparatus dispersion. Cos 1 (A, C) and Cos7 (B) cells were transfected with a GFP-FKBP control, or the GFP-LC8 or GFP-TcTex1 trap. Cells were then treated with AP20187 for 1 h (A) or 8 h (B, C). All cells were stained with DAPI to identify nuclei.

As tests for LC function, we evaluated the effects of the traps on early endosome, lysosome, and Golgi distribution, as well as mitotic progression. First, we fused green fluorescent protein (GFP) to the N-terminus of both FKBP-traps to identify transfected cells. Next, we transfected Cos1, Cos7, or HeLa cells with either trap or a GFP-FKBP control and labeled endosomes, lysosomes and Golgi with EEA1, LAMP2 and GM130 markers, respectively (FIGS. 12A-12C). Expression of the traps alone resulted in a moderate increase in the fraction of cells that exhibited evidence of organelle dispersal as compared to non-transfected cells or the GFP-FKBP control. The percentage of cells expressing the GFPLC8 or GFP-TcTex1 trap with dispersed endosomes was 14.7±1.5% and 13.3±1.5%, respectively, as compared to 11.7±3.5% and 10.3±3.5% for non-transfected cells and cells that expressed a GFP-FKBP control, respectively. This suggests that the LC8- and TcTex1-traps do not detectably affect the free pool of endogenous LCs. Treatment of non-transfected or GFPFKBP-expressing cells with AP20187 for 8 h did not affect the dispersion for each organelle. However, cells that expressed either trap and were treated with 100 μM AP20187 exhibited dramatic reorganization of early endosomes, lysosomes, and the Golgi apparatus (FIGS. 12A-12C). After 8 h of treatment with AP20187, we observed greater than 50% dispersion of the three organelle types for each trap.

To ensure the AP20187 concentration was not limiting, we followed the LC8-trap-induced dispersion of lysosomes as a function of AP20187 concentration after 8 h. The amount of lysosome dispersion increased with increasing AP20187 concentrations; however, it reached a plateau at 100 nM, and no further increase in lysosome dispersion was seen at higher AP20187 concentrations (data not shown). For the TcTex1-trap, we observed efficient endosome, lysosome and Golgi dispersion at AP20187 concentrations of 1 μM or greater. Non-transfected cells did not show dispersal of these organelles at any concentration of AP20187 tested (e.g., <2 μM).

As an alternative test to verify these observations, we monitored the distribution of Golgi in cells subjected to LC8 RNAi. We observed clear Golgi dispersal in a comparable fraction of cells as determined for LC trapping. After 3 days of treatment, 54%+2.5% of transfected cells showed Golgi dispersion, similar to the 8 h time point observed using either trap (data not shown). The level of Golgi dispersion in cells treated with a scrambled RNAi control was 12%+1.5%, which was similar to control experiments using only the LC8-trap. We also observed that the expression level of the dynein IC remained unaffected by the LC8 RNAi treatment (data not shown). These observed levels of Golgi dispersion are in agreement with recently reported levels of organelle dispersion using RNAi for both light chains.

Figure 13B:
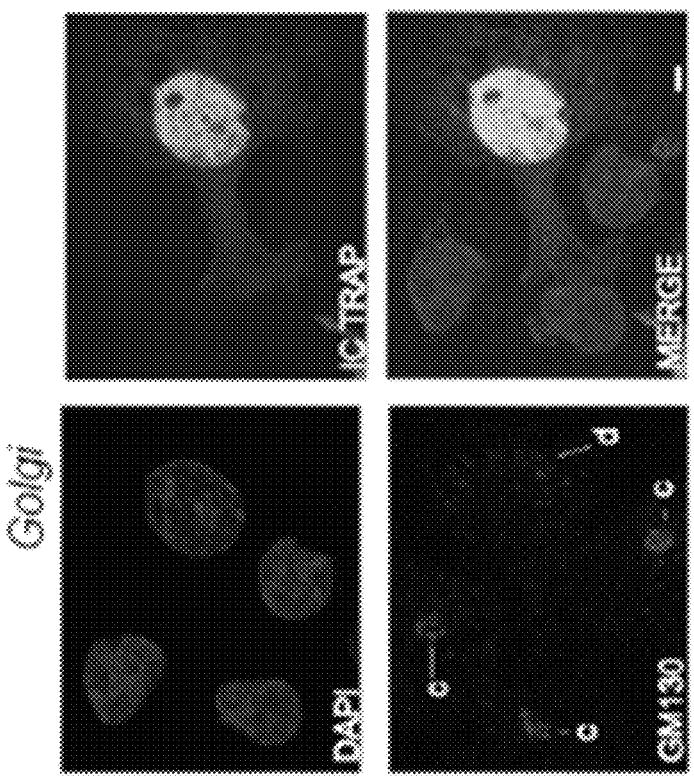
FIGS. 13A-13B depict that induction of IC traps leads to Endosome (FIG. 13A) and Golgi apparatus (FIG. 13B) dispersion. Cos1 cells were transfected with the GFP IC trap (upper rights panels of FIGS. 13A and 13B) for 24 h and then treated with AP20187 for 1 h. The cells were stained with DAPI for nuclei (upper left panels of FIGS. 13A and 13B) and EEA1 for endosomes (FIG. 13A, lower left panel)) or GM130 marker for Golgi bodies (FIG. 13B, lower left panel). Note the endosomes and Golgi apparatus are dispersed (marked "d") within 10 min and 1 h, respectively. Cells not containing the IC trap all show compact endosomes and Golgi bodies (marked "c"). Scale bar is 5 μm.
Figure 13A:
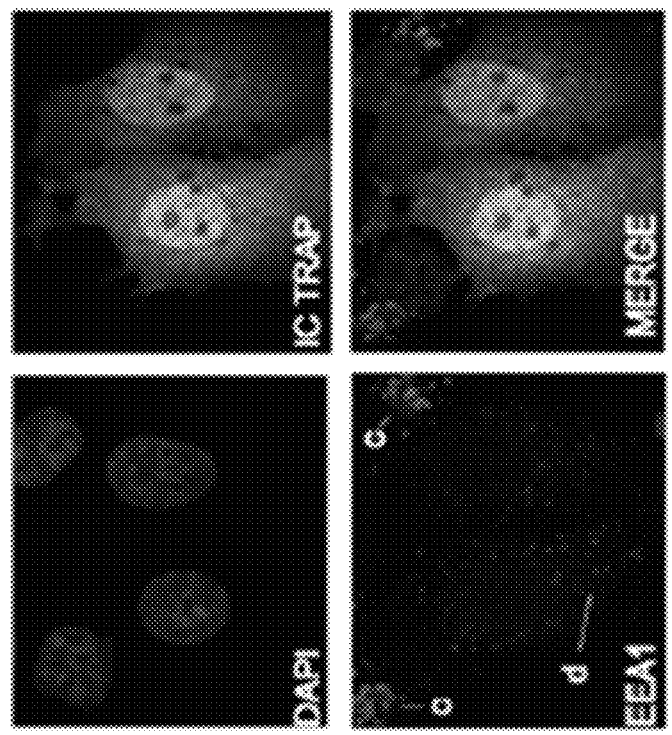
Figure 14A:
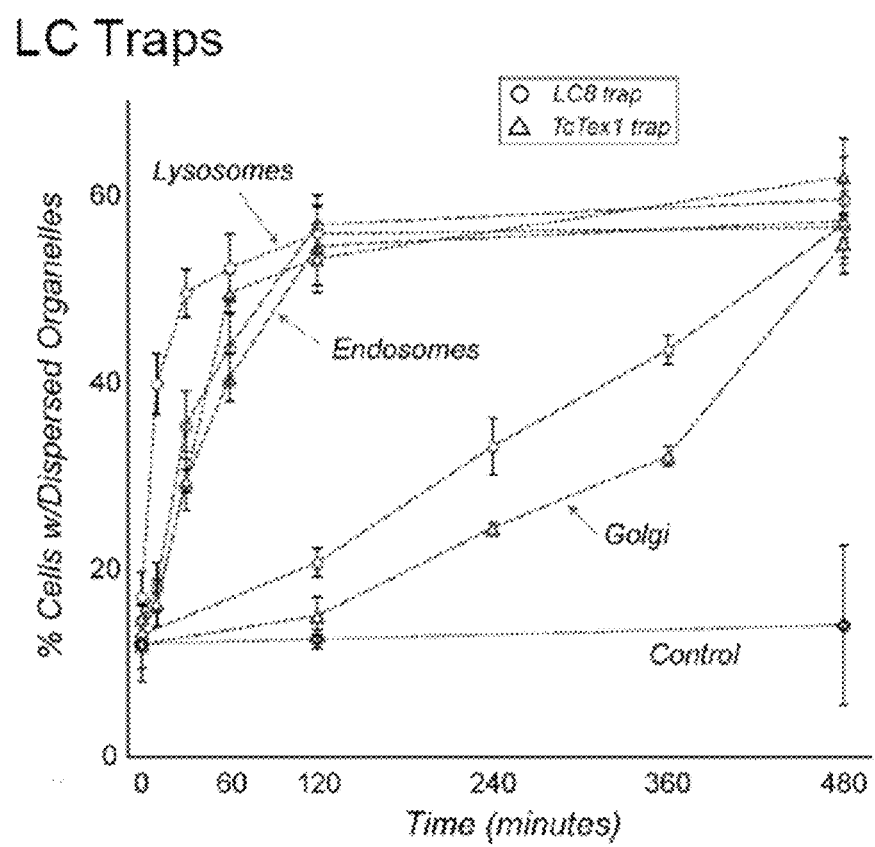
FIGS. 14A-14B depict the time course of vesicle dispersion by LC sequestration and IC competition.
Figure 14B:
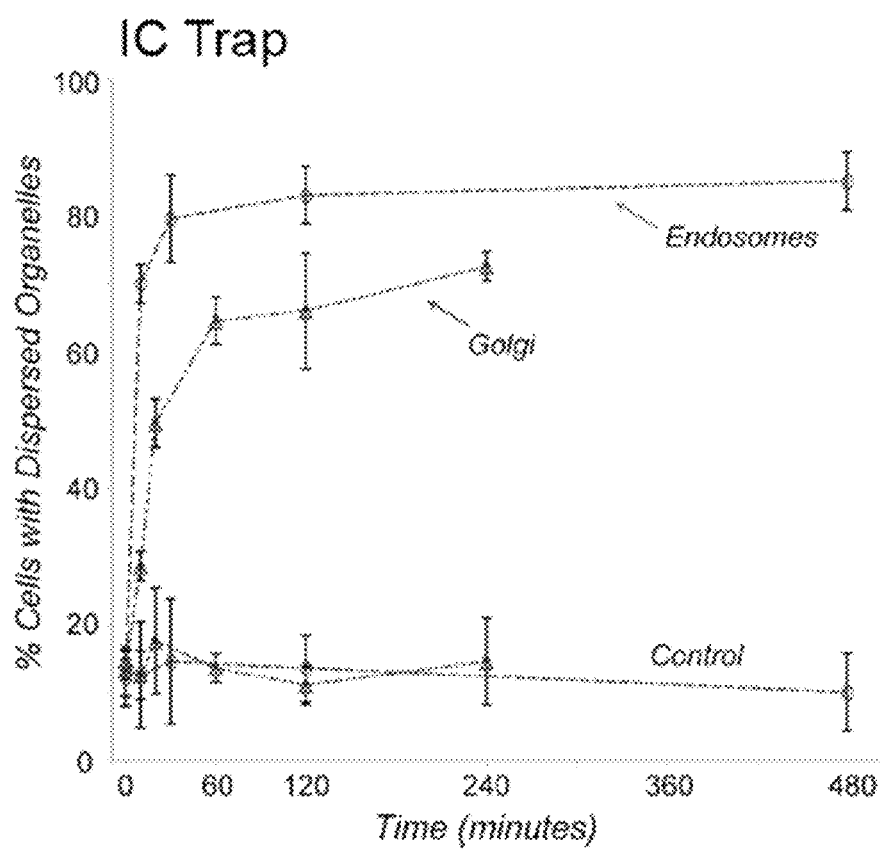

As a test for effects on cytoplasmic dynein functions that are distinct from vesicular transport, we monitored mitotic behavior in cells expressing either the LC8- or TcTex1-traps. We observed little effect on either mitotic index or the fraction of mitotic cells at discrete mitotic stages with either trap (data not shown). We did note a small increase in defective mitotic spindle morphology in cells transfected with the LC8-trap (20+2%), and cells transfected with RNAi compared to a control 11+3%) against LC8 (28+3%) recapitulated this result, suggesting this aspect of mitotic behavior was partially under LC8 control (data not shown). Finally, similar studies were carried out using the IC trap. As before, we observed little or no change in the dispersion of endosomes and Golgi apparatus before AP20187 treatment. Induction of dimerization through the addition of AP20187 (1 μM) produced immediate changes in both organelles. See FIGS. 13A-13B. After 4 h, 81+4% of cells contained dispersed endosomes and 68+3% of cells contained dispersed Golgi. The percentage of cells with dispersed organelles was significantly greater using the IC trap as compared to either LC trap (FIGS. 14A-14B). The precise reason for this difference is not clear; however, currently, we attribute this to a change in the cytoskeleton, but this must still be verified. We are also in the process of measuring the effect of sequestering the dynein IC on mitotic behavior.

Kinetic Analysis Separates Dynein Functions.

A major purpose for developing these traps is to provide immediate inhibition of protein function and follow the cellular response from this perturbation to gain new insight. Thus, we monitored the fraction of cells with dispersed organelles as a function of time. After induction of dimerization by AP20187, effects on both early endosome and lysosome distribution were detectable at 10 min, and leveled off at ~2 h (FIGS. 14A-14B). Intriguingly, these effects occurred at comparable rates with either the LC8 or TcTex1 trap. The most rapid effect was observed on lysosomes in cells expressing the LC8 trap. In striking contrast, Golgi dispersal using either trap occurred over a much longer time-course, requiring 8 h after induction of dimerization to reach similar levels of dispersion as for endosomes and lysosomes. Twenty-four hours after addition of AP20187, the percentage of cells with dispersed Golgi reached levels greater than 85%. The comparable effects of LC8- and TcTex1-traps on organelle distribution support their having a common effect on cytoplasmic dynein.

On the other hand, similar experiments using the IC trap indicate that the Golgi disperse much more rapidly compared to the LC traps (FIG. 14B). The IC trap also increases the rate of endosome dispersion. (FIG. 14B). Additional experiments, including live cell imaging, is necessary to fully address this difference, however, it is possible that this difference reflects the off-rate of the LCs (e.g., the LC traps sequester free LCs and the IC trap directly competes with the dynactin) or the loss of the microtubule architecture.

Microtubule Architecture.

Figure 15A:
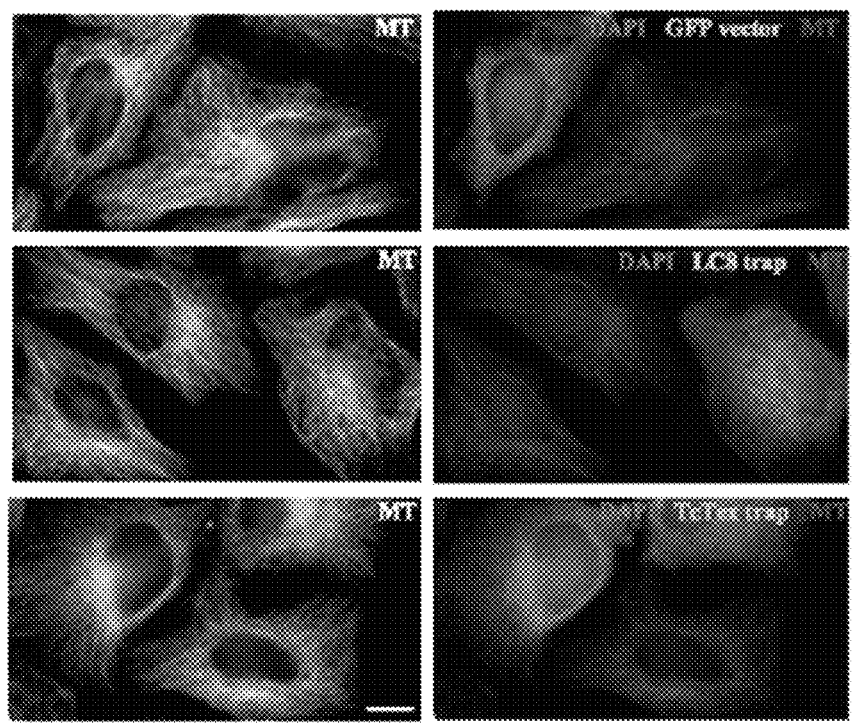
FIG. 15A depicts that the microtubule (MT) radial array is not affected by LC traps. Top panel shows cells transfected with a GFP-FKBP control. Middle and bottom panels show cells transfected with a LC8 trap and TcTex1 trap, respectively. MTs stained with anti-tubulin.
Figure 15B:
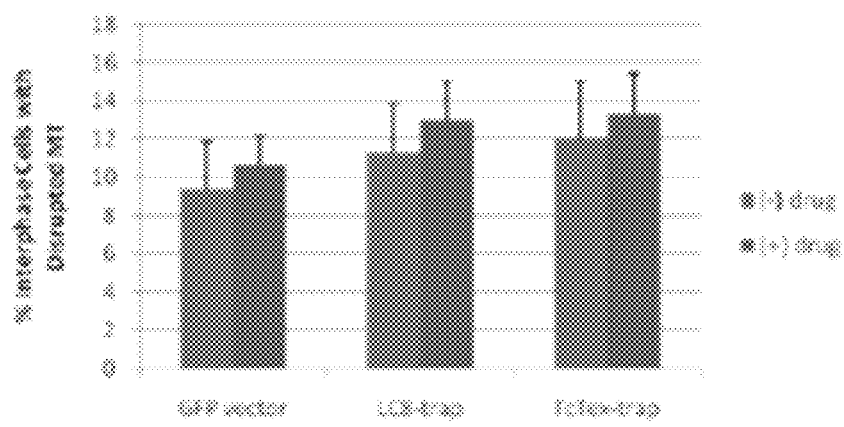
FIG. 15B: Graph shows percentage of cells with disrupted MTs 8 h post-induction with AP20187. No significant changes in the cytoskeleton were observed.
Figure 16B:
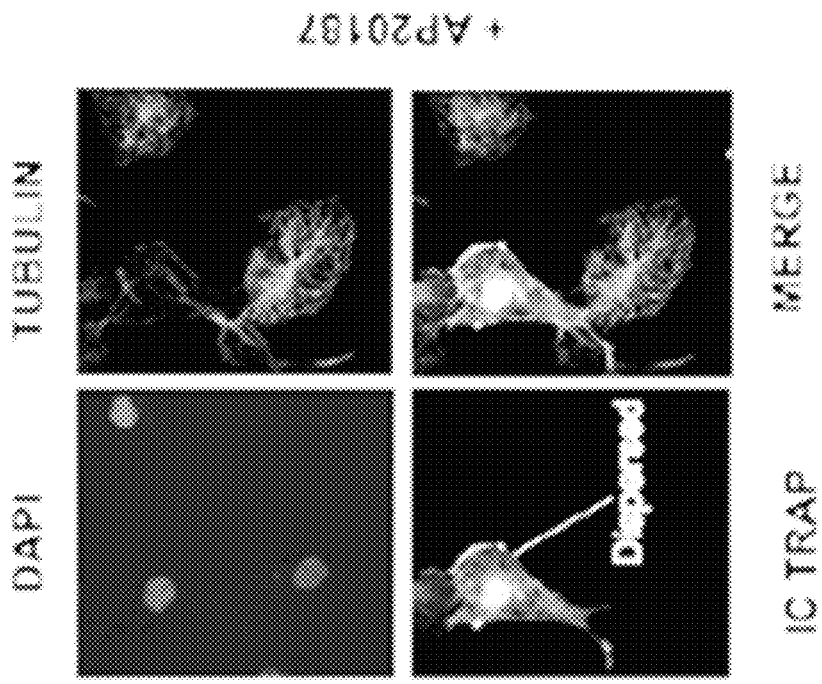
FIG. 16B: Addition of AP20187 to these cells affects the MT array (right four panels—fixed and stained 1 hour after the addition of AP20187).
Figure 16A:
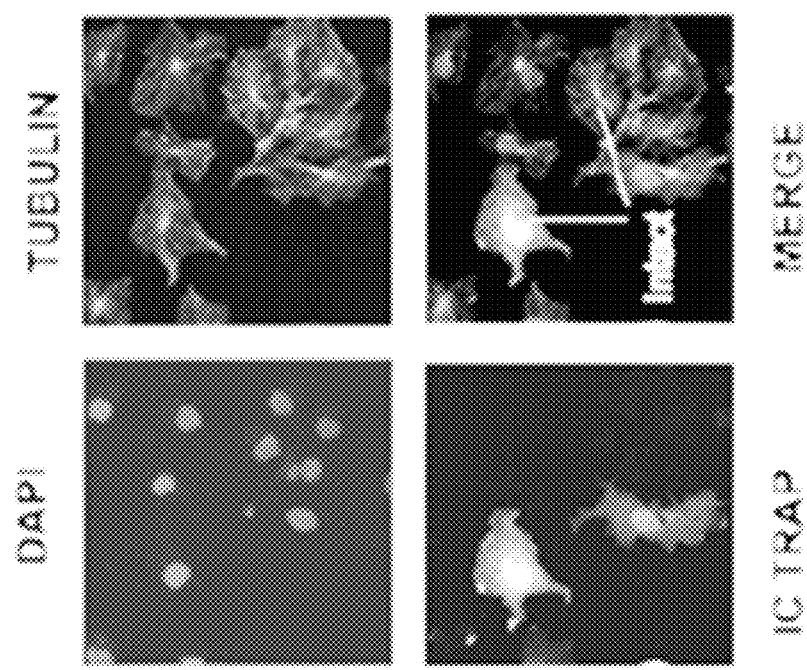
FIG. 16A depicts that blocking dynein IC affects the microtubule (MT) radial array. The left four panels show no affect on the MT radial array upon the expression of the IC trap and in the absence of AP20187. The MT array is stained with anti-α-tubulin. The nucleus is stained with DAPI.

Known methods of inhibiting cytoplasmic dynein, such as expression of dynactin polypeptides or RNAi against the dynein regulatory factors NudEL and ZW10, cause disorganization of the radial microtubule (MT) network in cultured mammalian cells 52-54. Despite observing clear dynein phenotypes (e.g., organelle dispersion), the microtubule network did not appear disorganized in cells subjected to LC trapping (FIGS. 15A-15B). On the other hand, the MT radial array was significantly disrupted upon AP20187-induced dimerization of the IC trap (FIGS. 16A-16B). This is consistent with previous studies where overexpressing a dimeric form of the IC trap (e.g., CC1 of p150glued) also disrupts of the MT array).

Summary.

These data demonstrate the power of the inducible molecular traps. We show traps that target different parts of the dynein complex differentially affect cellular processes (e.g., vesicles, MT array and mitosis). These observations are distinct from previous studies using siRNA, overexpression of dominant negatives, small molecule inhibitors of MTs and microinjection. In fact, for the majority of the studies previously carried out using these established methods (especially RNAi and expression of a dominant negative) the results would be indistinguishable (e.g., after 4 days RNAi against the LCs, ICs or dynactin would show same level of Golgi disruption).

V. Embodiments

Embodiment 1

A compound having the formula:

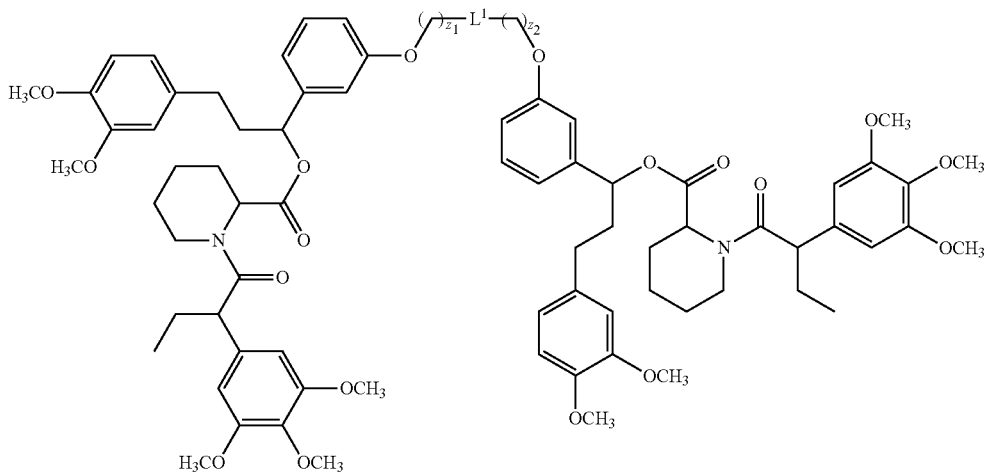

(I)

wherein, $L^1$ is a photocleavable linker, and $z_1$ and $z_2$ are each independently an integer in the range 0 to 6.

Embodiment 2

The compound of embodiment 1, wherein $L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

Embodiment 3

The compound of one of embodiments 1 to 2, wherein $L^1$ comprises a nitrophenylene.

Embodiment 4

The compound of one of embodiments 1 to 2 wherein $L^1$ has the formula: $-L^2-L^3-L^4-L^5-L^6-$ wherein, $L^2$ and $L^6$ are independently —C(O)O—; $L^3$ and $L^5$ are independently a bond or substituted or unsubstituted alkylene; $L^4$ is $R^1$-substituted arylene; and $R^1$ is an electron withdrawing group.

Embodiment 5

The compound of embodiment 4, wherein $R^1$ is halogen, —NO$_2$, —N$^+$(R$^2$)$_3$, —SR$^2$, —OR$^2$, —N(R$^2$)$_2$, —CF$_3$, —CCl$_3$, —CN, —SO$_3$R$^2$, —COOR$^2$, —CHO or —COR$^2$; and $R^2$ is hydrogen or an unsubstituted $C_1$ to $C_4$ alkyl.

Embodiment 6

The compound of embodiment 4 or 5, wherein $L^1$ is:

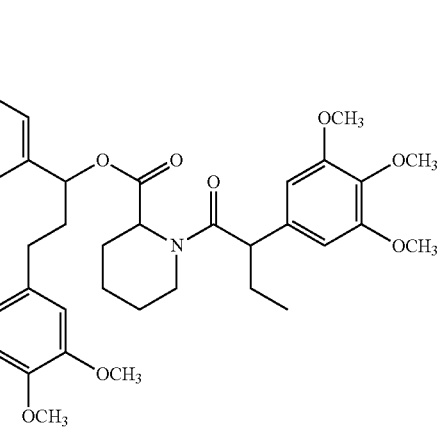

Embodiment 7

The compound of one of embodiments 4 to 6, wherein $L^3$ and $L^5$ are independently substituted or unsubstituted alkylene.

Embodiment 8

The compound of one of embodiments 4 to 6, wherein $L^3$ and $L^5$ are independently substituted or unsubstituted $C_1$ to $C_4$ alkylene.

Embodiment 9

The compound of one of embodiments 4 to 6, wherein $L^3$ and $L^5$ are independently substituted or unsubstituted $C_1$ to $C_3$ alkylene.

Embodiment 10

The compound of one of embodiments 4 to 6, wherein $L^3$ and $L^5$ are substituted with an unsubstituted $C_1$ to $C_4$ alkylene.

Embodiment 11

The compound of one of embodiments 4 to 6, wherein $L^3$ and $L^5$ are substituted with a methyl.

Embodiment 12

The compound of one of embodiments 4 to 6, wherein $L^3$ and $L^5$ are methylene substituted with an unsubstituted $C_1$ to $C_4$ alkylene.

Embodiment 13
The compound of one of embodiments 4 to 12, wherein L¹ is:
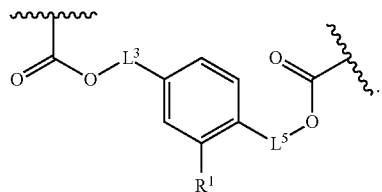
Embodiment 14
The compound of one of embodiments 4 to 13, wherein R¹ is NO₂.
Embodiment 15
The compound of embodiment 1 having the formula:
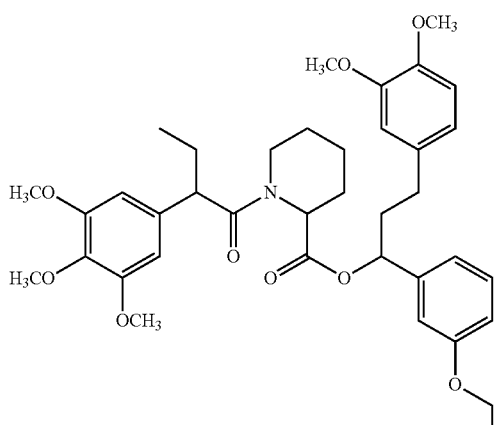
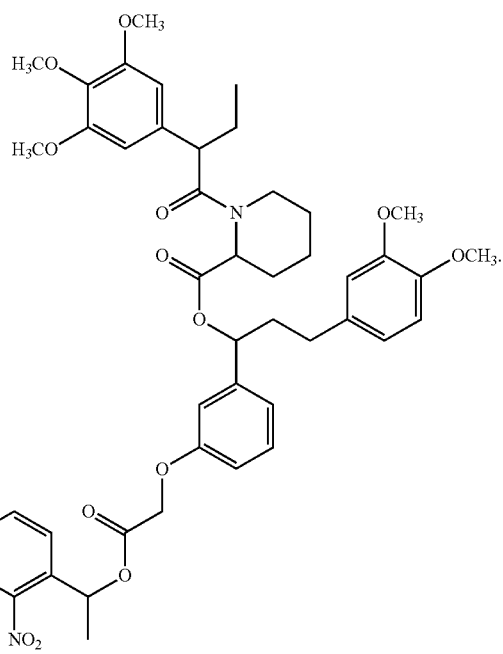
Embodiment 16
The compound of one of embodiments 1 to 14 having the formula:
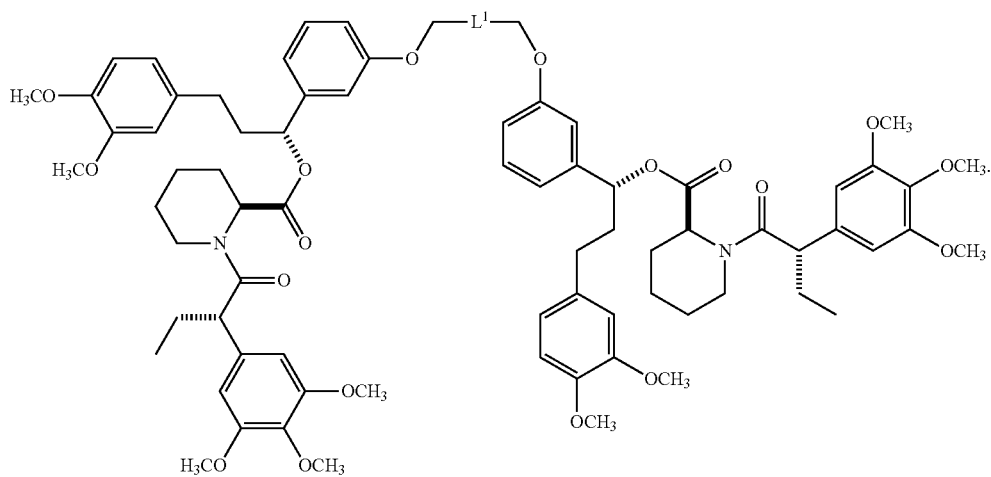

Embodiment 17

The compound of embodiment 1 having the formula:

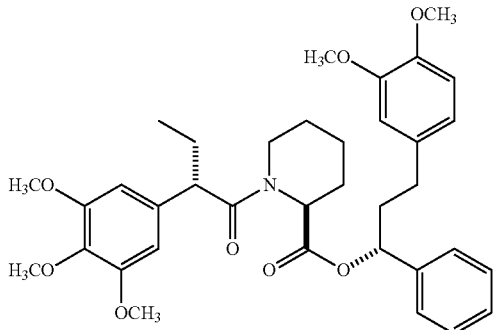
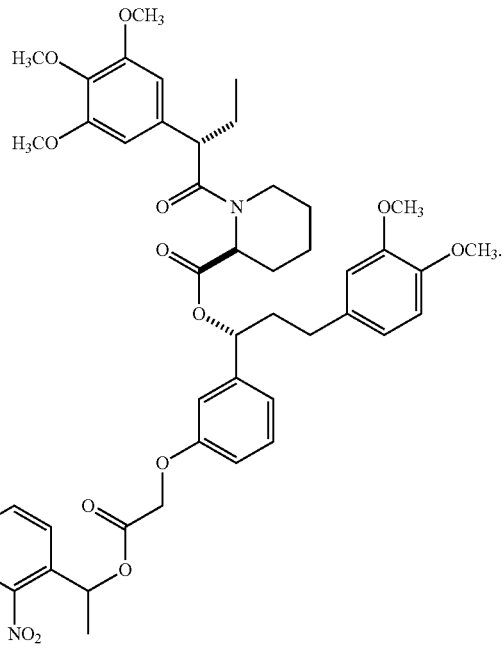

Embodiment 18

A method of forming an FK506 binding protein (FKBP) dimer, the method comprising: contacting a first FKBP and a second FKBP with the compound of one of embodiments 1 to 17; and allowing said compound to bind to said first FKBP and said second FKBP thereby forming an FKBP dimer comprising a link between said first FKBP and said second FKBP.

Embodiment 19

The method of embodiment 18, further comprising: exposing said FKBP dimer to a photon thereby cleaving said link.

What is claimed is:

1. A compound having the formula:

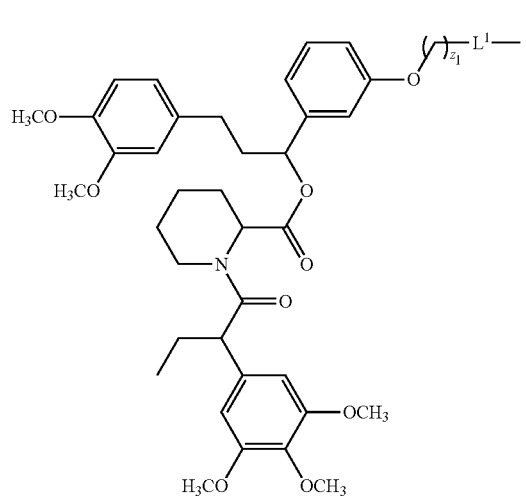

(I)

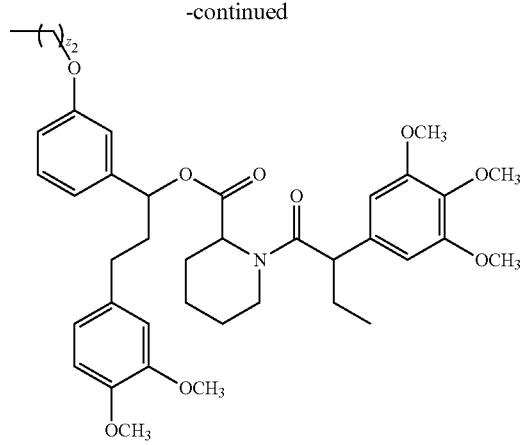

wherein,
$L^1$ is a photocleavable linker, and $z_1$ and $z_2$ are each independently an integer in the range 0 to 6.

2. The compound of claim 1, wherein
$L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

3. The compound of claim 1, wherein $L^1$ comprises a nitrophenylene.

4. The compound of claim 1, wherein $L^1$ has the formula:

-$L^2$-$L^3$-$L^4$-$L^5$-$L^6$- wherein $L^2$ and $L^6$ are —C(O)O;

$L^3$ and $L^5$ are independently a bond or substituted or unsubstituted alkylene;

$L^4$ is $R^1$-substituted arylene; and $R^1$ is an electron withdrawing group.

5. The compound of claim 4, wherein $R^1$ is halogen, —$NO_2$, $N^+(R^2)_3$, —$SR^2$, —$OR^2$, —$N(R^2)_2$, —$CF_3$, —$CCl_3$, —CN, —$SO_3R^2$, —$COOR^2$, —CHO or —$COR^2$; and $R^2$ is hydrogen or an unsubstituted $C_1$ to $C_4$ alkyl.

6. The compound of claim 4, wherein $L^1$ is:

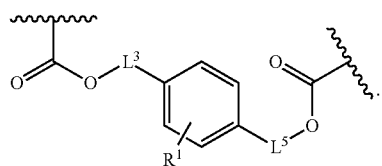

7. The compound of claim 4, wherein $L^3$ and $L^5$ are independently substituted or unsubstituted alkylene.

8. The compound of claim 4, wherein $L^3$ and $L^5$ are independently substituted or unsubstituted $C_1$ to $C_4$ alkylene.

9. The compound of claim 4, wherein $L^3$ and $L^5$ are independently substituted or unsubstituted $C_1$ to $C_3$ alkylene.

10. The compound of claim 4, wherein $L^3$ and $L^5$ are substituted with an unsubstituted $C_1$ to $C_4$ alkylene.

11. The compound of claim 4, wherein $L^3$ and $L^5$ are substituted with a methyl.

12. The compound of claim 4, wherein $L^3$ and $L^5$ are methylene substituted with an unsubstituted $C_1$ to $C_4$ alkylene.

13. The compound of claim 4, wherein $L^1$ is:

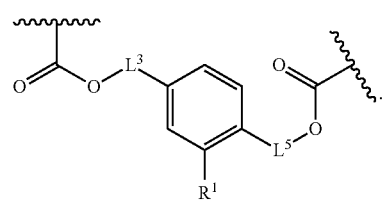

14. The compound of claim 4, wherein $R^1$ is $NO_2$.

15. The compound of claim 1 having the formula:

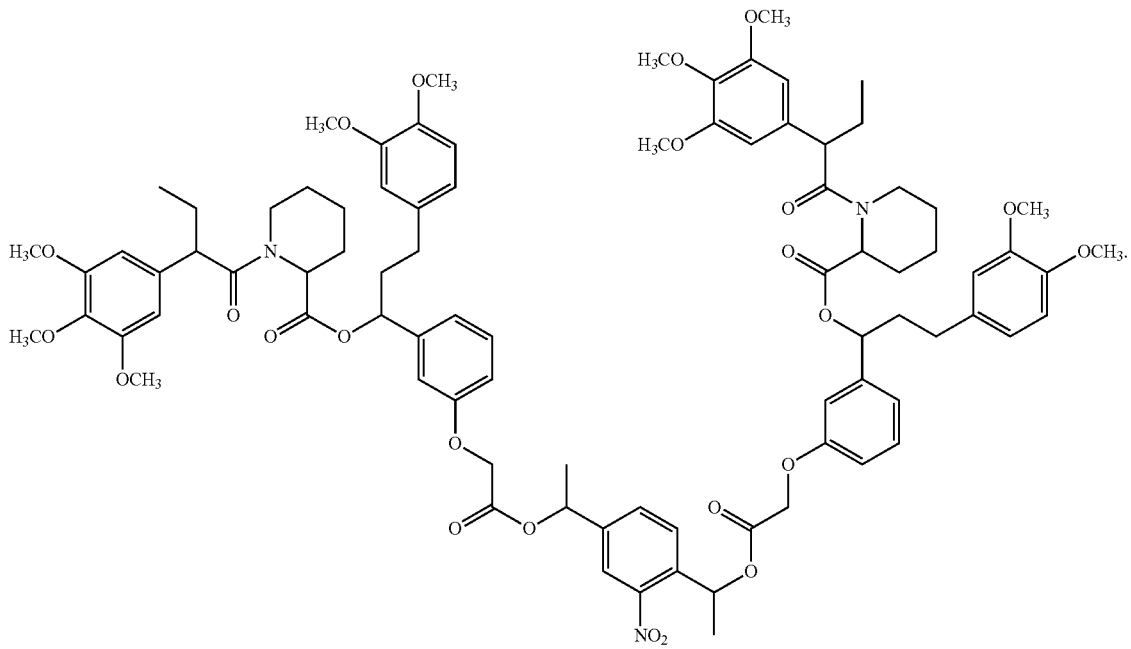 [SMILES: CCC(C(=O)N1CCCCC1C(=O)OC(CCc1ccc(OC)c(OC)c1)c1cccc(OCC(=O)OC(C)c2ccc(C(C)OC(=O)COc3cccc(C(CCc4ccc(OC)c(OC)c4)OC(=O)C4CCCCN4C(=O)C(CC)c4cc(OC)c(OC)c(OC)c4)c3)c([N+](=O)[O-])c2)c1)c1cc(OC)c(OC)c(OC)c1]

16. The compound of claim 1 having the formula:

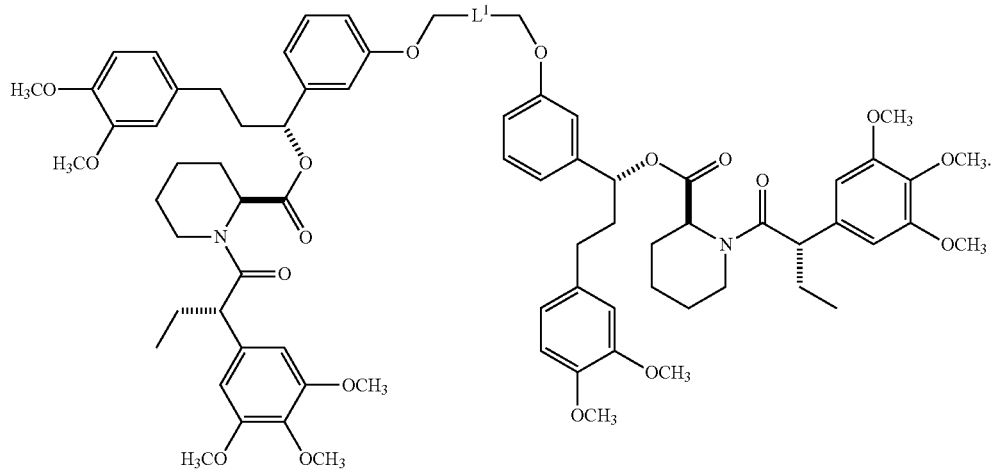

17. The compound of claim 1 having the formula:

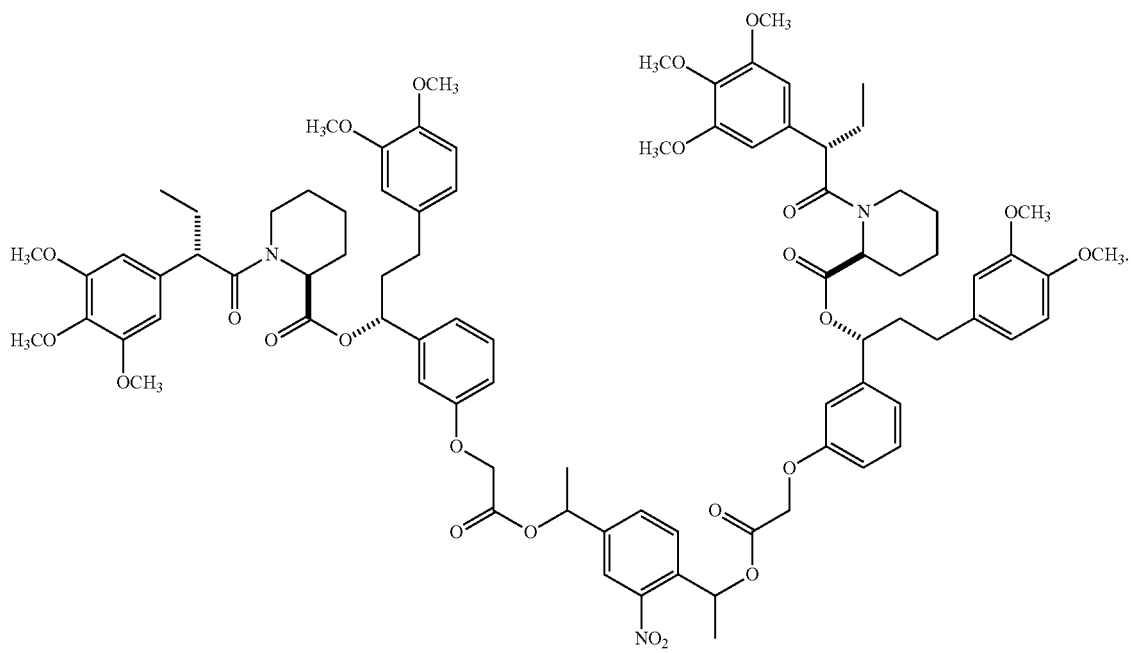

18. A method of forming an FK506 binding protein (FKBP) dimer, the method comprising:
(i) contacting a first FKBP and a second FKBP with the compound of claim 1; and
(ii) allowing said compound to bind to said first FKBP and said second FKBP thereby forming an FKBP dimer comprising a link between said first FKBP and said second FKBP.

19. The method of claim 18, further comprising:
(iii) exposing said FKBP dimer to a photon thereby cleaving said link.

* * * * *